US008652817B2

(12) United States Patent
Wood et al.

(10) Patent No.: US 8,652,817 B2
(45) Date of Patent: Feb. 18, 2014

(54) RECOMBINANT HOST CELLS AND MEDIA FOR ETHANOL PRODUCTION

(75) Inventors: Brent E. Wood, Gainesville, FL (US); Lonnie O. Ingram, Gainesville, FL (US); Lorraine P. Yomano, Gainesville, FL (US); Sean W. York, Gainesville, FL (US)

(73) Assignee: Univeristy of Florida Research Foundation, Inc., Gainesville, FL (US)

( * ) Notice: Subject to any disclaimer, the term of this patent is extended or adjusted under 35 U.S.C. 154(b) by 1036 days.

(21) Appl. No.: 11/922,631

(22) PCT Filed: Jun. 30, 2006

(86) PCT No.: PCT/US2006/025655
§ 371 (c)(1),
(2), (4) Date: Apr. 1, 2010

(87) PCT Pub. No.: WO2007/005646
PCT Pub. Date: Jan. 11, 2007

(65) Prior Publication Data
US 2010/0196978 A1 Aug. 5, 2010

Related U.S. Application Data

(60) Provisional application No. 60/696,076, filed on Jul. 1, 2005.

(51) Int. Cl.
*C12P 7/06* (2006.01)

(52) U.S. Cl.
USPC .................. 435/161; 435/252.3; 536/23.2

(58) Field of Classification Search
None
See application file for complete search history.

(56) References Cited

U.S. PATENT DOCUMENTS

| 3,816,251 | A | 6/1974 | Nakayama et al. |
| 5,405,764 | A | 4/1995 | Harder et al. |
| 7,026,152 | B2 * | 4/2006 | Ingram et al. ................. 435/210 |

OTHER PUBLICATIONS

Arntzen, C.E.; Dale, B.E. (co-chairs). Biobased Industrial Products, Priorities for Research and Commercialization. National Academy Press: Washington, D.C. 1999.
Zaldivar, J.; Nielsen J.; Olson L. Fuel Ethanol Production from Lignocellulose: a Challenge for Metabolic Engineering and Process Integration. Appl. Microbiol. Biotechnol. 2001, 56, 17-34.
Von Sivers M.; Zacchi G.; Olson L.; Hahn-Hagerdal B. Cost Analysis of Ethanol from Willow Using Recombinant *Escherichia coli*. Biotechnol. Prog. 1994, 10, 555-560.
Wyman, C.E. Potential Synergies and Challenges in Refining Cellulosic Biomass to Fuels, Chemicals, and Power. Biotechnol. Prog. 2003, 19, 254-262.

Ohta, K.; Beall D. S.; Mejia J.P.; Shanmugan K.T.; Ingram L.O. Metabolic Engineering of *Klebsiella oxytoca* M5A1 for Ethanol Production from Xylose and Glucose. Appl. Environ. Microbiol. 1991, 57, 2810-2815.
Wood, B.E.; Ingram L.O. Ethanol Production from Cellobiose, Amorphous Cellulose and Crystalline Cellulose by Recombinant *Klebsiella oxytoca* Containing Chromosomally Integrated *Zymomonas mobilis* Genes for Ethanol Production and Plasmids Expressing thermostable Cellulase Genes from *Clostridium thermocellum*. Appl. Environ. Microbiol. 1992, 58, 2103-2110.
Form PCT/ISA/237 (Written Opinion of the International Searching Authority), May 8, 2007, The University of Florida Research Foundation, Inc.
Form PCT/ISA/210 (International Search Report), May 8, 2007, The University of Florida Research Foundation, Inc.
Bothast, R.J.; Saha B.; Flosenzier A.V.; Ingram L.O. Fermentation of L-arabinose D-xylose and D-glucose by Ethanologenic Recombinant *Klebsiella oxytoca* strain P2. Biotechnol Lett. 1994, 16, 401-406.
Doran J.B.; Aldrich H.C.; Ingram L.O. Saccarification and Fermentation of Sugar-cane Bagasse by *Klebsiella oxytoca* P2 Containing Chromosomally Integrated Genes Encoding the *Zymomonas mobilis* Ethanol Pathway. Biotechnol. Bioengin. 1994, 44, 240-247.
Brooks, T.A.; Ingram L.O. Conversion of Mixed Waste Office Paper to Ethanol by Genetically Engineered *Klebsiella oxytoca* strain P2. Biotechnol. Prog. 1995, 11, 619-625.
Wood, B.E.; Aldrich H.C.; Ingram L.O. Ultrasound Stimulates Ethanol Production Druing the Simultaneous Saccharification and Fermentation of Mixed Waste Office Paper. Biotechnol. Prog. 1997, 13, 232-237.
Ohta, K.; Beall D.S.; Mejia J.P.; Shanmugam K.T.; Ingram L.O. Genetic Improvement of *Escherichia coli* for Ethanol Production: Chromosomal Integration of *Zymomonas mobilis* Genes Encoding Pyruvate Decarboxylase and Alcohol Dehydrogenase II. Appl. Environ. Microbiol. 1991, 57, 893-900.
Linsay, S.E.; Bothast R.J.; Ingram L.O. Improved Strains of Recombinant *Escherichia coli* of Ethanol Production from Sugar Mixtures. Appl. Microbiol. Biotechnol. 1995, 43, 70-75.
Yomano, L.P.; York S.W.; Ingram L.O. Isolation and Characterization of Ethanol Tolerant Mutants of *Escherichia coli* KO11 for Fuel Ethanol Production. J. Ind. Microbiol. 1998, 20, 132-138.
Burchhardt, G.; Ingram L.O. Conversion of Xylan to Ethanol by Ethanologenic Strains of *Escherichia coli* and *Klebsiella oxytoca*. Appl. Environ. Microbiol. 1992, 58, 1128-1133.

(Continued)

*Primary Examiner* — Jim Ketter
(74) *Attorney, Agent, or Firm* — Edwards Wildman Palmer LLP; Peter F. Corless; Jeffrey D. Hsi

(57) ABSTRACT

Disclosed are recombinant host cells suitable for degrading an oligosaccharide that have been optimized for growth and production of high yields of ethanol, and methods of making and using these cells. The invention further provides minimal media comprising urea-like compounds for economical production of ethanol by recombinant microorganisms. Recombinant host cells in accordance with the invention are modified by gene mutation to eliminate genes responsible for the production of unwanted products other than ethanol, thereby increasing the yield of ethanol produced from the oligosaccharides, relative to unmutated parent strains. The new and improved strains of recombinant bacteria are capable of superior ethanol productivity and yield when grown under conditions suitable for fermentation in minimal growth media containing inexpensive reagents. Systems optimized for ethanol production combine a selected optimized minimal medium with a recombinant host cell optimized for use in the selected medium. Preferred systems are suitable for efficient ethanol production by simultaneous saccharification and fermentation (SSF) using lignocellulose as an oligosaccharide source. The invention also provides novel isolated polynucleotide sequences, polypeptide sequences, vectors and antibodies.

8 Claims, 7 Drawing Sheets

(56) References Cited

OTHER PUBLICATIONS

Qian Y.; Yomano L.P.; Preston J.F.; Aldrich H.C.; Ingram L.O. Cloning, Characterization, and Functional Expression of the *Klebsiella oxytoca* Xylodextrin Utilization Operon (xyn TB) in *Escherichia coli*. Appl. Environ. Microbiol. 2003, 69, 5957-5967.

Kadam, K.L.; Newman M.M. Development of a Low-cost Fermentation Medium for Ethanol Production from Biomass. Appl. Microbiol. Biotechnol. 1997, 47, 625-629.

Ingram, L.O.; Gomez P.F.; Lai X.; Moniruzzanman M.; Wood B.E.; Yomano L.P.; York S.W. Metabolic Engineering of Bacteria for Ethanol Production. Biotechnol. Bioengin. 1998, 58, 204-214.

Zhang, J.; Greasham R. Chemically Defined Media for Commercial Fermentations. Appl. Microbiol. Biotechnol. 1999, 51, 407-421.

\* cited by examiner

RECOMBINANT HOST CELLS AND MEDIA FOR ETHANOL PRODUCTION

This application is the U.S. national phase application, pursuant to 35 U.S.C. §371, of PCT international application Ser. No. PCT/US2006/025655, filed Jun. 30, 2006, designating the United States and published in English on Jan. 11, 2007 as publication WO 2007/005646 A2, which claims priority to U.S. provisional patent application Ser. No. 60/696,076, filed Jul. 1, 2005. The entire contents of the aforementioned patent applications are incorporated herein by this reference.

RELATED APPLICATIONS

This application claims the benefit of U.S. provisional application Ser. No. 60/696,076, filed Jul. 1, 2005, the entire content of which is expressly incorporated herein by reference.

STATEMENT OF U.S. GOVERNMENT INTEREST

Funding for the present invention was provided in part by the Government of the United States under Grant Nos.: 01-35504-10669 from the U.S. Department of Agriculture, and FG02-96ER20222 from the U.S. Department of Energy. The Government of the United States has certain rights in and to the invention.

BACKGROUND

The use of ethanol as an automotive fuel provides a cleaner burning and renewable alternative to petroleum-based fuels [1]. Technology currently in use for ethanol production is based on edible crops such as sugar cane juice (molasses) and corn starch [2] that have alternative markets. The cost of these feedstocks has been estimated to represent 40% of total production costs [3]. In contrast, inedible lignocellulosic biomass is available at a cost competitive with petroleum [4]. The continued development of improved microorganisms for the conversion of lignocellulosic sugars into ethanol offers the potential to decrease dependence on petroleum and create new manufacturing opportunities from existing plant materials.

Ethanologenic strains of *Klebsiella oxytoca* have been developed [5, 6]. These strains have been shown to metabolize a variety of sugar monomers (such as glucose, xylose, and arabinose) derived from lignocellulosic biomass [5-7]. Such strains can function well in simultaneous saccharification and fermentation (SSF) processes with cellulose [8-10]. An ethanologenic strain of *K. oxytoca* known as *K. oxytoca* P2 has been described that contains genes from *Zymomonas mobilis* encoding pyruvate decarboxylase (pdc) and alcohol dehydrogenase (adhB), enzymes involved in converting oligosaccharides to ethanol. These genes are chromosomally integrated into the genome of strain P2.

In contrast to analogous strains of *Escherichia coli* [11-13], *K. oxytoca* has the native ability to metabolize many soluble products from lignocellulosic biomass, including cellobiose, cellotriose, xylobiose, xylotriose, and arabinosides [6, 14, 15]. The ability of *K. oxytoca* P2 to efficiently metabolize incompletely hydrolyzed products from lignocellulose at pH 5.2 (near optimal for fungal enzymes) provides an added advantage during simultaneous saccharification and fermentation (SSF) processes [8]. Under these conditions, *K. oxytoca* P2 required less than half of the fungal cellulase required by *Saccharomyces cerevisiae* to achieve equivalent fermentation rates and yields [9].

The availability of inexpensive industrial media for growth of ethanologenic bacteria that support high ethanol productivity and yield is essential for ethanol production from biomass feedstocks [17, 18]. However, unlike grain, hydrolysates of cellulosic biomass are inherently nutrient poor and must be supplemented [16]. Accordingly, previous use of *K. oxytoca* P2 for ethanol production has involved culture of the cells in complex growth media containing laboratory nutrients such as yeast extract and Difco Tryptone™. Unfortunately, it is impractical to use such nutrients for commercial production of commodity chemicals such as ethanol from lignocellulose.

To fully realize the potential of recombinant ethanologenic bacterial strains to serve as a source of ethanol, there is a clear need for new and improved strains of such bacteria that can efficiently produce ethanol while growing in inexpensive minimal media, and new media that can support these cells.

SUMMARY OF THE INVENTION

The invention relates to recombinant host cells that have been optimized for growth and production of high yields of ethanol, and methods of making and using these cells. The invention further relates to novel optimized media for economical production of ethanol by recombinant microorganisms.

During fermentation by microorganisms, sugar-containing substrates in the media are converted into ethanol and a variety of unwanted co-products. Recombinant cells in accordance with the invention are modified by genetic manipulation to control (e.g., down regulate) genes responsible for the production of one or more products other than ethanol, thereby increasing the yield of ethanol produced by these cells from the sugars, relative to unmutated parent strains. The new and improved strains of recombinant bacteria are capable of superior ethanol productivity and yield when grown under conditions suitable for fermentation in minimal growth media containing inexpensive reagents. Certain strains are optimized for superior ethanol production in particular embodiments of the optimized media. Systems optimized for ethanol production combine a selected optimized minimal medium and a recombinant host cell optimized for use in the selected medium. Preferred systems are suitable for efficient ethanol production by SSF using lignocellulose as a saccharide source.

Accordingly, one aspect of the invention is a recombinant host cell suitable for degrading a saccharide comprising:

(a) a heterologous polynucleotide sequence that codes for an enzyme that converts sugars to ethanol, wherein the host cell expresses the heterologous polynucleotide sequence at a sufficient functional level so as to facilitate production of ethanol as a primary fermentation product by the bacterium; and (b) a mutation in at least one polynucleotide sequence that codes for a protein in a metabolic pathway in the cell that produces a product other than ethanol from sugars, wherein the mutation results in increased ethanol production by the cell, as compared to ethanol production by the cell in the absence of the mutation. In some embodiments of the recombinant host cell, the mutation is a deletion, insertion, or base change mutation.

Recombinant host cells in accordance with the invention can be produced from any suitable host organism, including single-celled or multicellular microorganisms such as bacteria, fungi or yeast, and higher eukaryotic organisms including nematodes, insects, reptiles, birds, amphibians and mammals. Yeast host cells are derived, e.g., from *Saccharomyces, Schizosacharomyces, Hansenula, Pachyosolen, Kluyveromyces, Debaryomyces, Yarrowia,* and *Pichia*. Bacterial host cells are selected from Gram-positive and Gram-negative bacteria. Preferred Gram-negative bacteria are enteric bacteria such as strains of *Erwinia* and *Klebsiella*. Gram-positive bacterial host cells include *Bacillus, Geobacillus, Clostridium, Streptococcus,* and *Cellulomonas*.

In some embodiments of bacterial host cells in accordance with the invention, the heterologous polynucleotide sequence codes for alcohol dehydrogenase and/or pyruvate decarboxylase, enzymes involved in the conversion of sugars to ethanol.

Some embodiments of the recombinant cells are derived from *Klebsiella oxytoca*, which has the native ability to use urea as a nitrogen source. These strains are especially suitable host organisms for use in minimal media comprising urea-like compounds as a defined nitrogen source. One such suitable host strain is *Klebsiella oxytoca* strain P2 (ATCC 55307), which was deposited with the American Type Culture Collection, International Depositary Authority, 12301 Parklawn Drive, Rockville, Md. 28852, U.S.A., on Mar. 11, 1992.

As discussed above, recombinant host cells in accordance with the invention comprise a mutation in at least one polynucleotide sequence that codes for a protein in a metabolic pathway in the cell that produces a product other than ethanol from sugars. In various embodiments of the cells, the product other than ethanol is selected from formate, lactate, succinate, acetate, acetoin, butanediol, 2,3-butanediol, xylitol, butyrate, pyruvate, proprionate, isopropyl alcohol, 1-propanol, 2-propanol, propanediol, citrate, glutamate, and acetone.

In one embodiment of the recombinant cells, the metabolic pathway is the butanediol pathway. Co-products of sugar metabolism resulting from this pathway are acetoin and 2,3-butanediol, which are produced by the enzymes α-acetolactate decarboxylase and α-acetolactate synthase, respectively. Accordingly, in some embodiments, the cells include a mutation in at least one polynucleotide sequence that codes for an enzyme involved in the butanediol metabolic pathway. The mutated polynucleotide sequence can comprise a nucleotide sequence from a budA, budB, budR, or budC gene, or a homolog or functional variant thereof. Some embodiments comprise a deletion mutation in one or both of the budA and budB genes. The deletion mutation decreases or eliminates expression of at least one and preferably both of the enzymes α-acetolactate decarboxylase and α-acetolactate synthase in the cell, thereby increasing ethanol production by the cell, as compared to ethanol production by the cell in absence of the mutation.

Any of the above-described bacterial strains can be used to obtain the genes for genetic manipulation and in some embodiments to serve as hosts for reinsertion of DNA fragments comprising the altered gene sequences.

Some preferred embodiments of recombinant bacterial host cells in accordance with the invention are represented by *Klebsiella oxytoca* strains, including strains BW15 (NRRLB-30857), BW19 (NRRLB-30858), and BW21 (NRLLB-30859), which were deposited on Jun. 28, 2005 with the Agricultural Research Service Culture Collection (ARSCC) of the National Center for Agricultural Utilization Research (Peoria, Ill., USA).

In another aspect, the invention provides a method for producing ethanol from a source of saccharide. The saccharide source is contacted with a recombinant host cell according to the invention, as described above, to thereby produce ethanol from the source of saccharide.

The invention further provides a method for producing a recombinant host cell optimized for producing ethanol from a saccharide source. The method comprises:

(a) contacting a parent ethanologenic host cell with a selected medium and an oligosaccharide source, under conditions suitable for ethanol production by the parent cell;

(b) determining the level of ethanol produced from the saccharide source in the medium under the selected conditions;

(c) determining the level of at least one product other than ethanol produced from the saccharide source, to identify an undesirable co-product having increased expression in the medium under the selected conditions; and (d) mutating a polynucleotide sequence of a gene encoding a protein in a metabolic pathway that produces the undesirable co-product, wherein the mutation decreases or eliminates expression of at least one protein in the metabolic pathway, and increases ethanol production by the cell as compared to ethanol production by the parent cell in the absence of the mutation, thereby producing a recombinant host cell optimized for ethanol production from a saccharide source.

Some embodiments of the method further comprise producing an isolated polynucleotide fragment comprising a mutation of the gene; and introducing the mutated polynucleotide fragment into the parent cell. In some embodiments of the method, the mutation is a deletion, insertion, or base change mutation.

In some embodiments of the method, the cell is optimized for ethanol production in a minimal medium. Any suitable host cell as described above can be used as the parent host cell strain to be optimized by the method.

In yet another aspect, the invention provides novel minimal media that support growth and ethanol production by a recombinant host cell suitable for degrading a saccharide. A medium in accordance with the invention includes a defined nitrogen source; a complex nitrogen source such as corn steep liquor (CSL), yeast autolysate and/or extract, corn processing by-product, soy processing byproduct, or spent fermentation broth; a source of phosphate; and source of magnesium.

Some embodiments of the minimal media include a urea-like compound as a defined source of nitrogen. In various embodiments of urea-based minimal media in accordance with the invention, the concentration of urea nitrogen is from about 0.1 to 100 mM, preferably from about 2.0-20 mM, and more preferably from about 8-12 mM. Also contributing to low production cost, minimal media in accordance with the invention contain low levels of complex nitrogen sources, for example, corn steep liquor (CSL). In several embodiments, the concentration of CSL is from about 0.1-100 g $L^{-1}$, preferably from about 1-20 g $L^{-1}$, and more preferably from about 5-10 g $L^{-1}$.

Some embodiments of the minimal media are optimized to support growth and ethanol production by a recombinant host cell suitable for degrading a saccharide. For example, some media are optimized to support growth and ethanol production at acidic pH, making them suitable for use in simultaneous saccharification and fermentation (SSF).

Some media in accordance with the invention are optimized to support growth and ethanol production by recombinant host cells described herein, made according to the methods described above. One preferred embodiment is a medium optimized to support growth and ethanol production by recombinant strains of *Klebsiella oxytoca*.

Media in accordance with the invention can further comprise a source of saccharide. In some embodiments, the source of saccharide comprises lignocellulose. The use of urea-like compounds in the novel media of the invention is particularly advantageous due to its relatively low cost as a source of nitrogen, relative to proteinaceous sources such as peptone and also to small molecule sources of nitrogen, such as ammonia, commonly used in growth media for bacterial culture.

Also encompassed by the invention are isolated polynucleotide sequences, vectors comprising these sequences, and isolated polypeptide sequences. The sequences are useful for many purposes, including construction of recombinant host cells expressing isolated polynucleotide sequences in accordance with the invention, and construction of recombinant host cells comprising mutations in these sequences.

In various embodiments, the invention further provides isolated polypeptides. Thus, in one embodiment, the invention provides a fragment of a polypeptide comprising the amino acid sequence of SEQ ID NO:6 or 7, wherein the fragment comprises at least 15 contiguous amino acids of SEQ ID NO: 6 or 7.

Another embodiment is a naturally occurring allelic variant of a polypeptide comprising the amino acid sequence of SEQ ID NO:6 or 7, wherein the polypeptide is encoded by a nucleic acid molecule which hybridizes to a nucleic acid molecule consisting of SEQ ID NO:3 or 4 under stringent conditions.

Other embodiments include polypeptides encoded by a nucleic acid molecule comprising a nucleotide sequence which is at least 60% identical to a nucleic acid comprising the nucleotide sequence of SEQ ID NO:3 or 4; and polypeptides comprising an amino acid sequence which is at least 50% identical to the amino acid sequence of SEQ ID NO:6 or 7.

Another aspect of the invention is a vector comprising a deletion mutation in a polynucleotide sequence of a bacterial gene coding for at least one of an α-acetolactate decarboxylase and an α-acetolactate synthase protein. The vector is capable of decreasing or eliminating expression of the proteins when integrated into a bacterial host cell.

The invention further features antibodies, such as monoclonal or polyclonal antibodies, that specifically bind proteins/polypeptides of the invention.

In some embodiments, the mutated polynucleotide sequence is derived from genes selected from budA and budB of *Klebsiella* species. The polynucleotide sequence can comprise deletion mutations in both budA and budB.

A preferred vector of this type comprises deletion mutations in polynucleotide sequences of bacterial genes coding for α-acetolactate decarboxylase and α-acetolactate synthase proteins, wherein the vector is capable of decreasing or eliminating expression of these gene products when integrated into a bacterial host cell.

One embodiment of such a vector comprises a mutated budAB polynucleotide sequence that is at least 80% identical to SEQ ID NO:5. Another embodiment comprises a mutated budAB polynucleotide sequence that is at least 80% identical to SEQ ID NO:8.

Particular embodiments of vectors in accordance with the invention are plasmids, in which the polynucleotide sequences are derived from genes selected from budA and budB of *Klebsiella* species. Exemplary plasmids are designated herein as pLOI3310 or PLOI3313.

Yet a further aspect of the invention is a system optimized for ethanol production from a saccharide source by a recombinant host cell suitable for degrading a saccharide. The system comprises:

(a) a selected medium that supports optimal growth and ethanol production by the host cell under selected conditions;

(b) a saccharide source; and (c) a recombinant host cell optimized for ethanol production in the selected medium and conditions, the cell comprising:

a heterologous polynucleotide sequence that codes for an enzyme that converts sugars to ethanol, wherein said cell expresses said heterologous polynucleotide sequence at a sufficient functional level so as to facilitate production of ethanol as a primary fermentation product by said host cell; and a mutation in at least one polynucleotide sequence that codes for a protein in a metabolic pathway in the cell that produces a product other than ethanol from the saccharide source in the medium under the selected conditions, wherein the mutation decreases or eliminates expression of the protein, thereby increasing ethanol production by the host cell, as compared to ethanol production by the cell lacking the mutation, thereby optimizing ethanol production.

In one embodiment of the system, a fermentation reaction is conducted in a minimal medium. In some embodiments, the minimal medium is a urea-based medium as described above.

Any suitable recombinant host cell that is optimized for ethanol production in the selected medium in accordance with the invention can be used in the system.

In some embodiments of the system, the source of saccharide comprises lignocellulose.

In one system in accordance with the invention suitable for use in SSF using lignocellulose as a saccharide source, the selected medium is a minimal urea-based medium as described above, and the recombinant host cell is a strain of *Klebsiella oxytoca* comprising a deletion mutation in a gene coding for a protein in the butanediol pathway.

In yet another aspect, the invention provides a kit comprising a recombinant host cell as described above, packaged with instructions for using the recombinant host cell according to the methods or systems of the invention.

Other aspects and advantages of the invention are discussed below.

BRIEF DESCRIPTION OF THE DRAWINGS

FIG. 1 is a diagram showing vector constructs and steps used in the construction of a recombinant ethanologenic bacterium lacking budAB genes of the butanediol pathway, according to an embodiment of the invention.

FIGS. 2A and 2B show results in LB media and media containing ammonia nitrogen. Symbols: ∆-LB; O-M9+Fe; ■-0.5% CSL+M. FIGS. 2C and 2D show results in media with urea nitrogen. Symbols: O-U-M9+Fe; ■-U-0.5%; CSL+M; ●-OUM1. Standard errors are included for data with n≥3.

FIG. 4A shows growth; FIG. 4B shows ethanol production. Symbols: O-strain BW21 (ΔbudAB); ●-strain P2 (parent). Standard errors are included for data with n≥3. Improved ethanol production is achieved by the mutated strain lacking budAB genes, which are involved in competing metabolic pathways that produce products other than ethanol from sugar substrates.

DETAILED DESCRIPTION OF THE INVENTION

I. Definitions

Figure 1A:
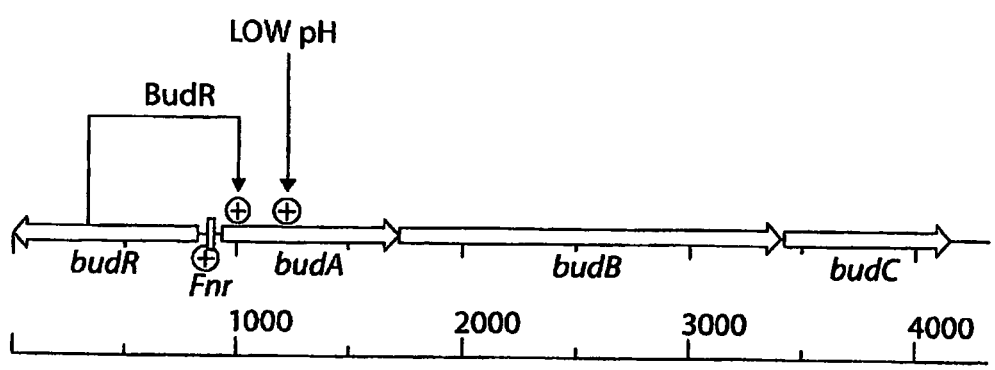
FIG. 1A is a schematic illustration showing operon and transcriptional regulation. Circled "+" signs denote that expression of the budAB operon is increased by low pH, and positively regulated by BudR and Fnr.

As used herein the terms "recombinant host cell," "recombinant microorganism," and the like, are intended to include cells suitable for, or subjected to, genetic manipulation, e.g., which can incorporate heterologous polynucleotide sequences, e.g., which can be transfected, or has been so manipulated. The cell can be a microorganism or a higher eukaryotic cell. The term is intended to include progeny of the cell originally transfected. In some embodiments, the cell is a bacterial cell, e.g., a Gram-positive bacterial cell or a Gram-negative bacterial cell. The latter term is intended to include all facultatively anaerobic Gram-negative cells of the family Enterobacteriaceae such as *Escherichia*, *Shigella*, *Citrobacter*, *Salmonella*, *Klebsiella*, *Enterobacter*, *Erwinia*, *Kluyvera*, *Serratia*, *Cedecea*, *Morganella*, *Hafnia*, *Edwardsiella*, *Providencia*, *Proteus*, and *Yersinia*. Preferred recombinant hosts are *Escherichia coli* or *Klebsiella oxytoca* cells.

The term "heterologous polynucleotide segment" or "heterologous polynucleotide sequence" is intended to include a polynucleotide segment that encodes one or more polypeptides or portions or fragments of polypeptides. A heterologous polynucleotide segment may be derived from any source, e.g., eukaryotes, prokaryotes, virii, or synthetic polynucleotide fragments. The term "heterologous polynucleotide sequence" may also refer to a polynucleotide sequence that is not naturally occurring in an organism, e.g., a sequence that is introduced into the organism. In one embodiment, the gene of a polynucleotide sequence is involved in at least one step in the bioconversion of a carbohydrate to ethanol. Accordingly, the term is intended to include any gene encoding a polypeptide such as an alcohol dehydrogenase, a pyruvate decarboxylase, a secretory protein/s, or a polysaccharase, e.g., a glucanase, such as an endoglucanase or exoglucanase, a cellobiohydrolase, β-glucosidase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, or pectate lyase.

The terms "polysaccharase," "cellulase," or "glucanase" are used interchangeably herein and are intended to include a polypeptide capable of catalyzing the degradation or depolymerization of any linked sugar moiety, e.g., disaccharides, trisaccharides, oligosaccharides, including complex carbohydrates, also referred to herein as complex sugars, e.g., cellooligosaccharide and lignocellulose, which comprise cellulose, hemicellulose, and pectin. The terms are intended to include cellulases such as glucanases, including, preferably, endoglucanases but also including, e.g., exoglucanase, β-glucosidase, cellobiohydrolase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination of any of these cellulases.

The term "endoglucanase" is intended to include a cellulase which typically hydrolyses internal β1-4 glucosyl linkages in polymeric substrates and does not preferentially hydrolyze linkages located at the ends of the chain.

The terms "saccharide," "saccharide source," "oligosaccharide source," "oligosaccharide," "complex cellulose," "complex carbohydrate," "complex sugar," "polysaccharide," "sugar source," "source of a fermentable sugar" and the like are intended to include any carbohydrate source comprising more than one sugar molecule.

The term "saccharide," as used herein, includes, e.g., disaccharides, trisaccharides, oligosaccharides, and polysaccharides. These carbohydrates may be derived from any unprocessed plant material or any processed plant material. Examples are wood, paper, pulp, plant derived fiber, or synthetic fiber comprising more than one linked carbohydrate moiety, i.e., one sugar residue.

One particular saccharide source is "lignocellulose," which represents approximately 90% of the dry weight of most plant material and contains carbohydrates, e.g., cellulose, hemicellulose, pectin, and aromatic polymers, e.g., lignin. Cellulose makes up 30%-50% of the dry weight of lignocellulose and is a homopolymer of cellobiose (a dimer of glucose). Similarly, hemicellulose makes up 20%-50% of the dry weight of lignocellulose and is a complex polymer containing a mixture of pentose (xylose, arabinose) and hexose (glucose, mannose, galactose) sugars which contain acetyl and glucuronyl side chains. Pectin makes up 1%-20% of the dry weight of lignocellulose and is a methylated homopolymer of glucuronic acid.

Other saccharide sources include carboxymethyl cellulose (CMC), amorphous cellulose (e.g., acid-swollen cellulose), and the cellooligosaccharides cellobiose, cellotriose, cellotetraose, and cellopentaose. Cellulose, e.g., amorphous cellulose may be derived from a paper or pulp source (including, e.g., fluid wastes thereof) or, e.g., agricultural byproducts such as corn stalks, soybean solubles, or beet pulp. Any one or a combination of the above carbohydrate polymers is a potential source of sugars for depolymerization and subsequent bioconversion to ethanol by fermentation according to the products and methods of the present invention.

The term "nucleic acid" is intended to include nucleic acid molecules, e.g., polynucleotide sequences which include an open reading frame encoding a polypeptide, and can further include non-coding regulatory sequences, and introns. Nucleic acid molecules in accordance with the invention include DNA molecules (e.g., linear, circular, cDNA or chromosomal DNA) and RNA molecules (e.g., tRNA, rRNA, mRNA) and analogs of the DNA or RNA generated using nucleotide analogs. The nucleic acid molecule can be single-stranded or double-stranded, but advantageously is double-stranded DNA.

An "isolated" nucleic acid molecule of the invention includes a nucleic acid molecule which is free of sequences which naturally flank the nucleic acid molecule (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of nucleotide sequences which naturally flank the nucleic acid molecule in chromosomal DNA of the microorganism from which the nucleic acid molecule is derived. Moreover, an isolated nucleic acid molecule, such as a cDNA molecule, can be substantially free of other cellular materials when produced by recombinant techniques, or substantially free of chemical precursors or other chemicals when chemically synthesized.

A "gene," as used herein, is a nucleic acid that can direct synthesis of an enzyme or other polypeptide molecule, e.g., can comprise coding sequences, for example, a contiguous open reading frame (ORF) which encodes a polypeptide, or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. One embodiment of a gene is one or more genes that map to a functional locus or operon such as the budA and budB genes of Klebsiella, that encode the proteins α-acetolactate decarboxylase and α-acetolactate synthase, respectively, which are involved in the butanediol metabolic pathway. In addition, the term "gene" is intended to include a specific gene for a selected purpose. A gene can be endogenous to the host cell or can be recombinantly introduced into the host cell, e.g., as a plasmid maintained episomally or a plasmid (or fragment thereof) that is stably integrated into the genome.

An "isolated gene," as described herein, includes a gene which is essentially free of sequences which naturally flank the gene in the chromosomal DNA of the organism from which the gene is derived (i.e., is free of adjacent coding sequences which encode a second or distinct polypeptide or RNA molecule, adjacent structural sequences or the like), and optionally includes 5' and 3' regulatory sequences, for example promoter sequences and/or terminator sequences. In one embodiment, an isolated gene includes predominantly coding sequences for a polypeptide (e.g., sequences which encode polypeptides).

The term "homolog," as used herein, includes a polypeptide or polypeptide sharing at least about 30-35%, advantageously at least about 35-40%, more advantageously at least about 40-50%, and even more advantageously at least about 60%, 70%, 80%, 90% or more identity with the amino acid sequence of a wild-type polypeptide or polypeptide described herein and having a substantially equivalent functional or biological activity as the wild-type polypeptide or polypeptide. Thus, the term "homolog" in intended to encompass "functional variants" as well as "orthologs" (equivalent genes from different species).

For example, a budA or budB homolog shares at least about 30-35%, advantageously at least about 35-40%, more advantageously at least about 40-50%, and even more advantageously at least about 60%, 70%, 80%, 90% or more identity with the polypeptide having the amino acid sequences set forth respectively as SEQ ID NO:6 and SEQ ID NO:7, and has a substantially equivalent functional or biological activity (i.e., is a functional equivalent) of the polypeptide having the amino acid sequence set forth as SEQ ID NO:6 or SEQ ID NO:7 (e.g., has a substantially equivalent α-acetolactate decarboxylase or α-acetolactate synthase activity). Methods for measuring functional activity of the gene product of a nucleic acid, or a homolog thereof in accordance with the invention are known, and are described in Examples below.

In one embodiment, the gene is involved in at least one step in the bioconversion of a carbohydrate to a product other than ethanol. Such products are also referred to herein as "co-products" or "co-products of fermentation." Co-products are generally undesirable in ethanol fermentation reactions, reducing yields as a result of diversion of the carbohydrate (saccharide) substrates into competing metabolic pathways other than those used for ethanol production. Accordingly, in one aspect, genes encoding proteins such as enzymes involved in the latter pathways (for instance, the butanediol pathway), are of interest in accordance with the invention as desired targets for elimination from the cells. Examples of genes involved in the bioconversion of a carbohydrate to a product other than ethanol in a microorganism are the budA and budB genes of bacteria, which respectively encode the enzymes α-acetolactate decarboxylase and α-acetolactate synthase involved in the synthesis of butanediol and acetoin from carbohydrate sources. Other genes of interest are those involved in metabolic pathways that produce other undesired co-products of sugar fermentation including but not limited to formate, lactate, succinate, acetate, acetoin, xylitol, butyrate, pyruvate, proprionate, isopropyl alcohol, 1-propanol, 2-propanol, propanediol, citrate, glutamate, and acetone.

"Allelic variant(s)," as used herein include both functional and non-functional proteins. Functional allelic variants will typically contain only conservative substitution of one or more amino acids of SEQ ID NO:6 or 7, or substitution, deletion or insertion of non-critical residues in non-critical regions of the protein. Non-functional allelic variants will typically contain a non-conservative substitution, a deletion, or insertion or premature truncation of the amino acid sequence of SEQ ID NO:6 or 7, or a substitution, insertion or deletion in critical residues or critical regions.

A polynucleotide or amino acid sequence of the present invention can further be used as a "query sequence" to perform a search against public databases, for example, to identify other family members or related sequences, e.g., genes related to budA and budB in organisms in which these genes have not been cloned. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to polynucleotide molecules of the invention. BLAST protein searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The term "mutation," as used herein, is intended to refer to a relatively permanent change in the hereditary material of an organism involving either an aberration in one or more chromosomes, or a change in the DNA sequence that makes up genes. A mutation, as used herein, includes a change in a DNA sequence created either by deletion or insertion of a DNA sequence, by a change in one or more bases (e.g., a point mutation), by duplication, by missense, by frameshift, by repeat or by nonsense mutation. Methods of creating insertion, deletion, and base change mutations are known in the art and are described, for example, in treatises such as Sambrook et al. [26].

The terms "fermentation" and "fermenting" are intended to include the degradation or depolymerization of a complex sugar and bioconversion of that sugar residue into ethanol, acetate and succinate. The terms are intended to include the enzymatic process (e.g. cellular or acellular, e.g. a lysate or purified polypeptide mixture) by which ethanol is produced from a carbohydrate, in particular, as a primary product of fermentation.

The term "simultaneous saccharification and fermentation" or "SSF" is intended to include the use of one or more recombinant hosts (or extracts thereof, including purified or unpurified extracts) for the contemporaneous degradation or depolymerization of a complex sugar and bioconversion of that sugar residue into ethanol by fermentation. SSF is a well-known process that can be used for breakdown of biomass to polysaccharides that are ultimately convertible to ethanol by bacteria. Reflecting the breakdown of biomass as it occurs in nature, SFF combines the activities of fungi (or enzymes such as cellulases extracted from fungi) with the activities of ethanologenic bacteria (or enzymes derived therefrom) to break down sugar sources such as lignocellulose to simple sugars capable of ultimate conversion to ethanol. SSF reactions are typically carried out at acid pH to optimize the use of the expensive fungal enzymes.

The term "transcriptional control" is intended to include the ability to modulate gene expression at the level of transcription. In a preferred embodiment, transcription, and thus gene expression, is modulated by replacing or adding a surrogate promoter near the 5' end of the coding region of a gene of interest thereby resulting in altered gene expression. In a preferred embodiment, the transcriptional control of one or more genes is engineered to result in the optimal expression of such genes, e.g., in a desired ratio. The term also includes inducible transcriptional control as recognized in the art.

The term "expression" is intended to include the expression of a gene at least at the level of mRNA production, and optionally at the polypeptide level.

The term "expression product" is intended to include the resultant product of an expressed gene, e.g., a polypeptide or protein.

The terms "increased expression" and "decreased expression" are intended to include an alteration in gene expression (up-regulation, and down-regulation, respectively) at least at the level of mRNA production, and preferably, at the level of polypeptide or protein expression.

The terms "increased production" and "decreased or eliminated production" in reference to a polypeptide are intended to include an increase or decrease in the amount of a polypeptide expressed, in the level of the enzymatic activity of the polypeptide, or a combination thereof.

The terms "activity" and "enzymatic activity" are used interchangeably and are intended to include any functional activity normally attributed to a selected polypeptide when produced under favorable conditions. The activity of an α-acetolactate decarboxylase enzyme (encoded by BudA) is, for example, to produce an acetoin product from a carbohydrate source. Techniques for determining activity such as that of α-acetolactate decarboxylase are known in the art (see for example Blomqvist et al. [35]), and are described in Examples herein.

The term "derived from" is intended to include the isolation (in whole or in part) of a polynucleotide segment from an indicated source, or the purification of a polypeptide from an indicated source. The term is intended to include, for example, direct cloning, PCR amplification, or artificial synthesis from, or based on, a sequence associated with the indicated polynucleotide source. In studies described herein, for example, nucleotide sequences encoding gene products involved in the butanediol pathway are derived from budA and budB genes amplified from the genomic DNA of the bacterium *Klebsiella oxytoca*.

The term "ethanologenic" is intended to include the ability of a microorganism to produce ethanol from a carbohydrate as a primary fermentation product. The term includes but is not limited to naturally occurring ethanologenic organisms, organisms with naturally occurring or induced mutations, and organisms that have been genetically modified.

The term "non-ethanologenic" is intended to include cells that are unable to produce ethanol from a carbohydrate as a primary non-gaseous fermentation product. The term is intended to include microorganisms that produce ethanol as the minor fermentation product comprising less than 40%, for example 20%, 30%, 40%, of total non-gaseous fermentation products.

The term "primary fermentation product" is intended to include non-gaseous products of fermentation that comprise greater than about 40%, 50%, 60%, 70%, 80%, 85%, 90%, 91%, 92%, 93%, 94%, 95% of total non-gaseous product. The primary fermentation product is the most abundant non-gaseous product. In certain embodiments of the invention, the primary fermentation product is ethanol. In further embodiments, the primary fermentation products are produced by the host grown in minimal salts medium.

The term "minor fermentation product" as used herein is intended to include non-gaseous products of fermentation that comprise less than 40%, for example 20%, 30%, 40%, of total non-gaseous product.

The terms "Gram-negative bacteria" and "Gram-positive bacteria" are intended to include the art-recognized definitions of these terms. Typically, Gram-negative bacteria include, for example, the family Enterobacteriaceae which comprises *Escherichia, Shigella, Citrobacter, Salmonella, Klebsiella, Enterobacter, Erwinia, Kluyvera, Serratia, Cedecea, Morganella, Hafnia, Edwardsiella, Providencia, Proteus,* and *Yersinia*. Other Gram-negative bacteria include, but are not limited to, *Acinetobacter, Gluconobacter, Geobacter* and *Shewanella*. Gram-positive bacteria include, but are not limited to, *Bacillus, Geobacillus, Clostridium, Streptococcus, Cellulomonas, Corynebacterium, Lactobacillis, Lactococcus, Oenococcus* and *Eubacterium*.

The term "defined nitrogen source" is intended to mean a discrete nitrogen source, i.e., a single chemical entity that is capable providing a source of nitrogen that is suitable for use in accordance with the invention. Exemplary defined nitrogen sources include, for example, urea and ammonia. In certain embodiments, two or more defined nitrogen sources may be used.

The term "complex nitrogen source", as distinguished from "defined nitrogen source" is intended to include a mixture of chemical entities that collectively provide sources of nitrogen that is suitable for use in accordance with the invention.

The term "urea" refers to an organic chemical compound having the formula $(NH_2)_2 CO$. The term "urea-like compound," as used herein, includes various analogs/derivatives of urea having the general formula $R_1N-(C=O)-_NR_2$. Urea-like compounds, and methods of making these compounds, are described, for example, in U.S. Pat. No. 6,875,764 to Muzi et al., (2005), the disclosure of which is hereby incorporated by reference in its entirety.

II. Recombinant Host Cells Comprising Mutations in Genes Encoding Proteins in Metabolic Pathways Leading to Byproducts of Fermentation As discussed, the invention relates to new and improved recombinant host cells suitable for degrading saccharides. The cells comprise mutations in one or more genes associated with a metabolic pathway for production of unwanted co-products of fermentation. Perturbation of these pathways results in a greater percentage of the saccharide starting materials being converted into ethanol, rather than other, undesired products of fermentation.

Accordingly and in one aspect, the invention provides a recombinant host cell suitable for degrading a saccharide. The cell comprises a heterologous polynucleotide sequence that codes for an enzyme that converts sugars to ethanol. The host cell expresses the heterologous polynucleotide sequence at a sufficient functional level so as to facilitate production of ethanol as a primary fermentation product. The recombinant host cell further comprises a mutation in at least one polynucleotide sequence that codes for a protein in a metabolic pathway in the cell that produces a product other than ethanol from the sugar source. The presence of the mutation decreases or eliminates expression of at least one protein in the metabolic pathway, thereby increasing ethanol production by the cell, as compared to ethanol production by the recombinant cell in absence of the mutation.

The recombinant host cell suitable for degrading saccharides can be a cell of a higher eukaryotic organism such as a nematode, an insect, a reptile, a bird, an amphibian, or a mammal. The cell can also be a cell of a single-celled or multi-cellular microorganism, such as a bacterium, yeast or fungus. Recombinant yeast cells in accordance with the invention are derived, e.g., from *Saccharomyces, Schizosaccharomyces, Hansenula, Pachyosolen, Kluyveromyces, Debaryomyces, Yarrowia,* and *Pichia*.

Some bacterial host cells in accordance with the invention are derived from Gram-positive bacteria. Certain embodiments of the cells are derived, e.g., from *Bacillus, Geobacillus, Clostridium, Streptococcus,* and *Cellulomonas*.

Other bacterial host cells are derived from Gram-negative bacteria. In some embodiments, the bacteria are facultatively anaerobic. Preferred facultative anaerobes are selected from the family Enterobacteriaceae, and include but are not limited to *Escherichia, Shigella, Citrobacter, Salmonella, Klebsiella, Enterobacter, Erwinia, Kluyvera, Serratia, Cedecea, Morganella, Hafnia, Edwardsiella, Providencia, Proteus,* and *Yersinia*.

As discussed, recombinant host cells in accordance with the invention comprise one or more heterologous polynucleotide sequences that code for an enzyme that converts sugars to ethanol. Accordingly, these cells are ethanologenic. Suitable polynucleotide sequences for use in constructing recombinant ethanologenic host cells may encode, e.g., genes from naturally occurring ethanologenic strains of bacteria, such as *Zymomonas mobilis*. Two preferred heterologous genes that convert sugars to ethanol include alcohol dehydrogenase (adh) and pyruvate decarboxylase (pdc). The recombinant cells of the invention include one or both of these genes and may further include other heterologous nucleotide sequences that code for enzymes such as polysaccharases that assist in converting sugar to ethanol. Preferably the heterologous genes are integrated into the bacterial chromosome.

Methods of making recombinant ethanologenic microorganisms are known in the art of molecular biology. Suitable materials and methods and recombinant host organisms are described, for example, in U.S. Pat. Nos. 6,849,434; 6,333,181; 5,821,093; 5,482,846; 5,424,202; 5,028,539; 5,000,000; 5,487,989, 5,554,520, and 5,162,516, hereby incorporated by reference, and may be employed in carrying out the present invention.

In some embodiments, the recombinant host cell is an ethanologenic Gram-negative bacterium from the family Enterobacteriaceae. The ethanologenic hosts of U.S. Pat. No. 5,821,093, hereby incorporated by reference, for example, are suitable hosts and include, in particular, *E. coli* strains KO4 (ATCC 55123), KO11 (ATCC 55124), and KO12 (ATCC 55125), and *Klebsiella oxytoca* strain P2 (ATCC 55307), discussed infra. Alternatively, a non-ethanologenic host of the present invention may be converted to an ethanologenic host by addition of heterologous polynucleotide sequences that code for one or more suitable enzymes that convert sugars to ethanol.

In some embodiments of the invention, a recombinant ethanologenic bacterial host cell is derived from *Erwinia* or *Klebsiella*. Recombinant hosts derived from *Klebsiella oxytoca* are particularly suitable for SSF of lignocellulose, having several advantages including efficiency of pentose and hexose co-fermentation, resistance to toxins, production of enzymes for complex saccharide depolymerization (avoiding or reducing the need for depolymerization by added fungal cellulases) and environmental hardiness.

One suitable ethanologenic *Klebsiella* host cell is *K. oxytoca* P2, a derivative of *K. oxytoca* M5A1 (See Wood, et al. (1992)*Appl. Environ. Microbiol.* 58:2103-2110, and U.S. Pat. No. 5,821,093). Advantageously, *K. oxytoca* strains possess the native ability to use urea as a nitrogen source. In one embodiment, the recombinant ethanologenic bacterium contains at least one heterologous polynucleotide segment (e.g., celY or celZ derived from *Erwinia*) encoding at least one endoglucanase (e.g., EGY or EGZ). More preferably, the recombinant ethanologenic host cell contains more than one heterologous polynucleotide segment which encodes endoglucanases. For example, as described in published U.S. Patent Application No. 2004/015990, celY and celZ can be functionally integrated, expressed, and secreted from the ethanologenic strain *K. oxytoca* P2 concurrently to produce ethanol from a saccharide substrate (e.g., crystalline cellulose).

As discussed above, it is known that the process of ethanol production by SSF is accompanied by the production of unwanted co-products of fermentation other than ethanol by recombinant host cells. Diversion of the substrate sugars into alternative metabolic pathways that produce products other than ethanol results in lower productivity and yield of ethanol than theoretically possible in the absence of the alternative pathways. Recombinant host cells in accordance with the invention are engineered to reduce this problem by virtue of their reduced capacity or inability to produce the unwanted co-products. Various embodiments of the cells are engineered such that the cells have reduced or absent capacity to produce selected co-products of fermentation. Some embodiments of the recombinant host cells are unable to produce co-products including but not limited to formate, lactate, succinate, acetate, acetoin, butanediol, 2,3-butanediol, xylitol, butyrate, pyruvate, proprionate, isopropyl alcohol, 1-propanol, 2-propanol, and acetone.

To effect the above-described inability to produce unwanted co-products, some embodiments of recombinant host cells in accordance with the invention comprise a deletion mutation in at least one polynucleotide sequence that codes for a protein in a metabolic pathway in the cell that produces a product other than ethanol from a sugar source. Some embodiments of the cells have deletion mutations in polynucleotide sequences that code for a protein involved in at least one metabolic pathway that produces formate, lactate, succinate, acetate, acetoin, butanediol, 2,3-butanediol, xylitol, butyrate, pyruvate, proprionate, isopropyl alcohol, 1-propanol, 2-propanol, or acetone from sugar in the cell.

One aspect of the invention involving deletion mutations relates to "knocking out" genes known to be associated with selected metabolic pathways in cells. Understanding is well advanced of the biochemical pathways that exist in cells, such as bacterial cells, to produce selected products of metabolism. Metabolic pathways that exist in cells such as bacteria for the production of products other than ethanol from sugars (e.g., products such as formate, lactate, succinate, acetate, acetoin, and 2,3-butanediol) have been described and can be readily ascertained, for example, by a search of the scientific literature.

Knockout of genes encoding proteins or functional fragments thereof involved in the metabolic pathways for production of formate, lactate, succinate, acetate, acetoin, butanediol, 2,3-butanediol, xylitol, butyrate, pyruvate, proprionate, isopropyl alcohol, 1-propanol, 2-propanol, or acetone results in recombinant hosts with inability to produce such unwanted co-products of sugar fermentation.

In some embodiments of the recombinant host cells, a deletion mutation is in at least one polynucleotide sequence that codes for an enzyme involved in the butanediol metabolic pathway. This pathway results in the production of acetoin and 2,3-butanediol from sugar sources by bacterial cells. In some embodiments, the deletion mutation is in one or both of the budA and budB genes, which respectively encode the enzymes α-acetolactate decarboxylase and α-acetolactate synthase. Production of these co-products by the butanediol pathway is brought about by the actions of these two enzymes. The deletion mutation decreases or eliminates expression of these enzymes, resulting in a recombinant ethanologenic host cell that is unable to produce acetoin and 2,3-butanediol from a sugar source, and which thereby exhibits increased ethanol production from the sugar source, relative to the recombinant cell in absence of the mutation.

One embodiment of a host cell provided by the invention is a recombinant ethanologenic bacterium comprising a deletion mutation in both the budA and budB genes. One preferred host cell carrying deletions in these genes is a variant of *K. oxytoca* P2 designated *K. oxytoca* BW21. As shown below, this strain can be advantageously used for ethanol production in minimal media containing urea-like compounds as a nitrogen source, and is particularly suitable for use in fermentation reactions conducted in media in the acidic pH range.

III. Isolated Nucleic Acid Molecules and Polypeptides

In another aspect, the present invention features isolated nucleic acid molecules comprising budA and budB gene sequences, which respectively encode the enzymes α-acetolactate decarboxylase and α-acetolactate synthase. The nucleic acids are derived from Gram-negative and Gram-positive bacteria, for example, the Gram-negative bacterium *Klebsiella oxytoca*.

Also featured are isolated genomic nucleic acids comprising the above-mentioned genes of the butanediol pathway (i.e., budA, budB) but also other flanking regions which comprise regulatory regions (e.g., promoter(s) and ribosome binding sites(s)) as well as other associated genes involved in ethanologenesis, e.g., alcohol dehydrogenase (adh) and pyruvate decarboxylase (pdc).

As discussed, the invention provides novel nucleic acids encoding, inter alia, full-length or partial coding sequences, respectively, of budA and budB genes from *Klebsiella* strains. These genes were isolated in response to the discovery of increased production of unwanted co-products of fermentation that result from the activity of enzymes encoded by these genes. More specifically, it was demonstrated that production of these co-products was increased in ethanologenic bacteria during fermentation reactions carried out in desirable, inexpensive growth media such as OUM described above.

To eliminate production of these product, a genetic strategy was devised to eliminate the ability of an ethanologenic producer cell to make the co-products. In one example, the genes encoding budA and a portion of budB were first cloned from *Klebsiella oxytoca*. The isolated sequences were subsequently subjected to genetic manipulation to delete a large fragment of the budAB gene, rendering it inoperative. The budA and budB genes had not been previously isolated from *Klebsiella oxytoca*. Accordingly, the invention provides in one aspect novel DNA sequences, and predicted amino acid sequences based on these DNA sequences.

One embodiment of a novel nucleic acid in accordance with the invention is an isolated nucleic acid molecule comprising the nucleotide sequence set forth in SEQ ID NO:3 or 4. The nucleic acid designated herein as SEQ ID NO:3 corresponds to a putative full-length coding sequence from the budA gene of *Klebsiella oxytoca*, which encodes the protein product α-acetolactate decarboxylase. The nucleic acid designated herein as SEQ ID NO:4 corresponds to a partial coding sequence from the budB gene of the same species, which encodes the protein α-acetolactate synthase.

Other novel sequences of the invention are predicted amino acid sequences corresponding to SEQ ID NOS:3 and 4, (described infra), which are designated herein as SEQ ID NOS:6 and 7, respectively.

One nucleic acid embodiment in accordance with the invention is an isolated nucleic acid molecule which encodes a polypeptide comprising the amino acid sequence set forth in SEQ ID NO:6 or 7.

The invention further provides an isolated nucleic acid molecule which encodes a naturally occurring allelic variant of a polypeptide comprising the amino acid sequence set forth in SEQ ID NO: 6 or 7.

In another embodiment, an isolated nucleic acid molecule encodes a homolog of a polypeptide comprising the amino acid sequence set forth in SEQ ID NO: 6 or 7. Additional budA and budB nucleic acid sequences are those that encode a homolog of the polypeptide having the amino acid sequence set forth in SEQ ID NO:6 or SEQ ID NO:7 (e.g., encoding a polypeptide having at least 30%, 40%, 50%, 60%, 70%, 80%, 90%, 95% or more identity to the polypeptide having the amino acid sequence as set forth in SEQ ID NO:6 or SEQ ID NO:7, and having a substantially identical activity as the polypeptide).

Yet other embodiments include the following isolated nucleic acid molecules: One embodiment is a nucleic acid molecule comprising a nucleotide sequence which is at least 60% identical to the nucleotide sequence of SEQ ID NO:3 or 4, or a complement thereof. In various embodiments, an isolated nucleic acid molecule of the present invention comprises a nucleotide sequence which is at least about 60-65%, advantageously at least about 70-75%, more preferably at least about 80-85%, and even more advantageously at least about 90-95% or more identical to a nucleotide sequence set forth herein as SEQ ID NO:3 or SEQ ID NO:4.

Yet another embodiment is a nucleic acid molecule comprising a fragment of at least 100 nucleotides of a nucleic acid comprising the nucleotide sequence of SEQ ID NO:3 or 4, or a complement thereof.

A nucleic acid molecule in accordance with the invention can also be one that encodes a polypeptide comprising an amino acid sequence at least about 50% identical to the amino acid sequence of SEQ ID NO:6 or 7.

Another embodiment is a nucleic acid molecule which encodes a fragment of a polypeptide comprising the amino acid sequence of SEQ ID NO: 6 or 7, wherein the fragment comprises at least 15 contiguous amino acid residues of the amino acid sequence of SEQ ID NO: 6 or 7.

In another embodiment, an isolated nucleic acid molecule hybridizes under stringent conditions to a nucleic acid molecule having a nucleotide sequence as set forth as SEQ ID NO:3 or SEQ ID NO:4. In another embodiment, an isolated budA or budB nucleic acid molecule hybridizes to all or a portion of a nucleic acid molecule having a nucleotide sequence that encodes a polypeptide having the amino acid sequence of SEQ ID NO:6, or SEQ ID NO:7.

Suitable hybridization conditions are known to those skilled in the art and can be found, e.g., in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11.

A particular, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A particular, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A particular, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM NaH$_2$PO$_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete.

The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M).

It will also be recognized by the skilled practitioner that additional reagents can be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or, alternatively, 0.2×SSC, 1% SDS).

In another embodiment, an isolated nucleic acid molecule comprises a nucleotide sequence that is complementary to a budA or budB nucleotide sequence as set forth herein (e.g., is the complement of the nucleotide sequence set forth as SEQ ID NO:3 or SEQ ID NO:4).

Yet another embodiment of the present invention features mutant budA or budB nucleic acid molecules or genes. Typically, a mutant nucleic acid molecule or mutant gene, as described herein, includes a nucleic acid molecule or gene having a nucleotide sequence which includes at least one alteration (e.g., base change, insertion, deletion) such that the polypeptide or peptide that can be encoded by said mutant exhibits an activity that differs from the polypeptide or peptide encoded by the wild-type nucleic acid molecule or gene.

One embodiment of an isolated mutant nucleic acid molecule in accordance with the invention comprises the mutated budAB nucleotide sequence from *Klebsiella oxytoca* set forth in SEQ ID NO:5. In another version of a nucleic acid comprising a mutated *Klebsiella* budAB nucleotide sequence, mutated (truncated) budA and budB coding sequences are separated by a tetracycline gene flanked by FRT sites, inserted between the mutated budA and budB genes. A DNA construct comprising the latter configuration is designated herein as SEQ ID NO:8. See also Examples 4 and 5, infra.

A nucleic acid molecule of the present invention (e.g., a nucleic acid molecule having the nucleotide sequence of SEQ ID NO:3 or SEQ ID NO:4) can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989) or can be isolated by the polymerase chain reaction using synthetic oligonucleotide primers designed based upon the sequence of SEQ ID NO:3 or SEQ ID NO:4. Primers suitable for the amplification of a DNA fragment from *Klebsiella oxytoca* and related strains comprising the putative full-length coding sequence of budA and a partial coding sequence of budB can have the nucleotide sequences set forth herein as SEQ ID NOS:1 and 2. A nucleic acid of the invention can be amplified using cDNA, mRNA or alternatively, genomic DNA, as a template and appropriate oligonucleotide primers according to standard PCR amplification techniques. Suitable PCR primers can be designed, for example, having the sequences of SEQ ID NOS: 1 and 2.

A mutant nucleic acid molecule or mutant gene can encode a polypeptide having improved α-acetolactate decarboxylase or α-acetolactate synthase activity, e.g., substrate affinity; thermostability; activity at a different pH; or codon usage (e.g., for improved expression in the recipient host cell).

Alternatively, a mutant nucleic acid molecule or mutant gene in accordance with the invention can encode a polypeptide having reduced or absent α-acetolactate decarboxylase or α-acetolactate synthase activity: A mutant nucleic acid encoding a mutated budAB polypeptide derived from *Klebsiella oxytoca* that lacks expression or activity of α-acetolactate decarboxylase and α-acetolactate synthase can have the sequence of SEQ ID NO:5 or 8. Methods for detecting reduced or absent α-acetolactate decarboxylase or α-acetolactate synthase activity are known, and described, for instance, in Examples, infra.

The invention further includes an isolated nucleic acid molecule comprising any of the above-described nucleic acid molecules and a nucleotide sequence encoding a heterologous polypeptide. In some embodiments, heterologous polynucleotide sequences of the present invention feature nucleic acids comprising isolated pyruvate decarboxylase (pdc) nucleic acid sequences or genes, and/or isolated alcohol dehydrogenase (adh) nucleic acid sequences or genes, derived from a Gram-positive or Gram-negative bacterium. Advantageously, the pdc nucleic acid or gene is derived from a Gram-negative microorganism selected from the group consisting of *Gluconobacter, Rhizobium, Bradyrhizobium, Alcaligenes, Rhodobacter, Rhodococcus. Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas* (e.g., *Zymomonas mobilis*), *Zymobacter* (e.g., *Zymobacter palmae*), and *Acetobacter* (e.g., *Acetobacter pasteurianus*).

In another embodiment, the pdc nucleic acid or gene is derived from a Gram-positive microorganism selected from the group consisting of *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas,* and *Sarcina* (e.g., *Sarcina ventriculi*).

As discussed above, another aspect of the present invention features novel isolated polypeptides (e.g., isolated enzymes active in the butanediol metabolic pathway, for example, α-acetolactate decarboxylase or α-acetolactate synthase derived from *Klebsiella oxytoca*. In one embodiment, polypeptides are produced by recombinant DNA techniques and can be isolated from microorganisms of the present invention by an appropriate purification scheme using standard polypeptide purification techniques. In another embodiment, polypeptides are synthesized chemically using standard peptide synthesis techniques.

An isolated or purified polypeptide (e.g., an isolated or purified α-acetolactate decarboxylase or α-acetolactate synthase) is substantially free of cellular material or other contaminating polypeptides from the microorganism from which the polypeptide is derived, or substantially free from chemical precursors or other chemicals when chemically synthesized. In one embodiment, an isolated or purified polypeptide has less than about 30% (by dry weight) of contaminating polypeptide or chemicals, more advantageously less than about 20% of contaminating polypeptide or chemicals, still more advantageously less than about 10% of contaminating polypeptide or chemicals, and most advantageously less than about 5% contaminating polypeptide or chemicals.

In one embodiment, an isolated polypeptide of the present invention (e.g., an isolated α-acetolactate decarboxylase or an isolated α-acetolactate synthase enzyme), comprises an amino acid sequence as shown in SEQ ID NO:6 or SEQ ID NO:7, respectively.

In other embodiments, an isolated polypeptide of the present invention is a homolog of at least one of the polypeptides set forth as SEQ ID NO:6 or SEQ ID NO:7 (e.g., comprises an amino acid sequence at least about 30-40% identical, advantageously about 40-50% identical, more advantageously about 50-60% identical, and even more advantageously about 60-70%, 70-80%, 80-90%, 90-95% or more identical to the amino acid sequence of SEQ ID NO:6 or SEQ ID NO:7, and has an activity that is substantially similar to that of the polypeptide encoded by the amino acid sequence of SEQ ID NO:6 or SEQ ID NO:7, respectively.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), advantageously taking into account the number of gaps and size of said gaps necessary to produce an optimal alignment.

The comparison of sequences and determination of percent identity between two sequences can be accomplished using a mathematical algorithm. A particular, non-limiting example of a mathematical algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (1997) *Nucleic Acids Research* 25(17):3389-3402. When utilizing BLAST and Gapped BLAST programs, the default parameters of the respective programs (e.g., XBLAST and NBLAST) can be used. See http://www.ncbi.nlm.nih.gov. Another particular, non-limiting example of a mathematical algorithm utilized for the comparison of sequences is the algorithm of Myers and Miller (1988) *Comput Appl Biosci.* 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

In another embodiment, the percent identity between two amino acid sequences can be determined using the GAP program in the GCG software package, using either a Blossom 62 matrix or a PAM250 matrix, and a gap weight of 12, 10, 8, 6, or 4 and a length weight of 2, 3, or 4. In yet another embodiment, the percent homology between two nucleic acid sequences can be accomplished using the GAP program in the GCG software package (available at http://www.gcg.com), using a gap weight of 50 and a length weight of 3.

IV. Vectors

The present invention further features vectors (e.g., recombinant vectors), including plasmid vectors. Vectors in accordance with the invention include nucleic acid molecules (e.g., isolated or recombinant nucleic acid molecules and/or genes) described herein. In particular, recombinant vectors are featured that include nucleic acid sequences that encode bacterial gene products as described herein, advantageously budA and budB gene products (e.g., SEQ ID NO:3 or 4) or mutated budA and budB sequences (e.g., SEQ ID NO:5 or 8) that reduce or eliminate expression of these gene products in host cells. The sequences are more advantageously budA and budB gene products of a Gram-negative or a Gram-positive bacterium, and even more advantageously budA and budB gene products derived from *Klebsiella* or *Erwinia*.

One embodiment of a vector in accordance with the invention includes a polynucleotide sequence comprising a mutation in a bacterial gene coding for at least one of an α-acetolactate decarboxylase and an α-acetolactate synthase protein, wherein the vector is capable of decreasing or eliminating expression of said protein when integrated into a bacterial host cell.

In one embodiment of the vector, the polynucleotide sequence comprises a mutation in an isolated nucleic acid molecule comprising the nucleotide sequence set forth in SEQ ID NO:3 or 4, or a functional fragment thereof, as discussed supra. The mutation can be a deletion, insertion or base change mutation.

In one preferred embodiment, the mutation in the polynucleotide sequence is a deletion mutation. Some versions of a vector of this type comprise a mutated budAB polynucleotide sequence from *Klebsiella oxytoca* as set forth in SEQ ID NO:5 or 8. Other vectors comprise a mutation in a polynucleotide sequence that is at least 80% identical to SEQ ID NO:5 or 8.

Another preferred embodiment of a vector in accordance with the invention is a plasmid vector comprising the mutated budAB polynucleotide sequence set forth in SEQ ID NO:5 or 8. Examples of plasmid vectors of this type, which have been designated pLOI3310 or pLOI3313, are described herein. See, for instance Examples 4 and 5, infra.

Another embodiment of a vector in accordance with the invention comprises the polynucleotide sequence set forth in SEQ ID NO:3, that encodes the protein α-acetolactase decarboxylase derived from *Klebsiella oxytoca*.

The recombinant vector (e.g., plasmid, phage, phasmid, virus, cosmid or other purified nucleic acid vector) can been altered, modified or engineered such that it contains greater, fewer or different nucleic acid sequences than those included in the native or natural nucleic acid molecule from which the recombinant vector was derived. Advantageously, the recombinant vector includes a budA and budB gene or recombinant nucleic acid molecule including a budA and budB gene or mutant thereof, operably linked to regulatory sequences, for example, promoter sequences, terminator sequences and/or artificial ribosome binding sites (RBSs), as defined herein.

Typically, the budA and budB gene or mutant is operably linked to a regulatory sequence(s) in a manner which allows for expression (e.g., enhanced, increased, constitutive, basal, attenuated, decreased or repressed expression) of the nucleotide sequence, advantageously expression of a gene product encoded by the nucleotide sequence (e.g., when the recombinant nucleic acid molecule is included in a recombinant vector, as defined herein, and is introduced into a microorganism).

The regulatory sequence includes nucleic acid sequences that affect (e.g., modulate or regulate) expression of other nucleic acid sequences. In one embodiment, a regulatory sequence is included in a recombinant nucleic acid molecule or recombinant vector in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule or recombinant vector operably linked to a regulatory sequence that accompanies or is adjacent to the gene of interest in the natural organism (e.g., operably linked to "native" regulatory sequences, for example, to the "native" promoter). Alternatively, a gene of interest can be included in a recombinant nucleic acid molecule or recombinant vector operably linked to a regulatory sequence that accompanies or is adjacent to another (e.g., a different) gene in the natural organism.

Alternatively, a gene of interest can be included in a recombinant nucleic acid molecule or recombinant vector operably linked to a regulatory sequence from another organism. For example, regulatory sequences from other microbes (e.g., other bacterial regulatory sequences, bacteriophage regulatory sequences, and the like) can be operably linked to a particular gene of interest.

In one embodiment, a regulatory sequence is a non-native or non-naturally-occurring sequence (e.g., a sequence which has been modified, mutated, substituted, derivatized, or deleted, including sequences which are chemically synthesized). Advantageous regulatory sequences include promoters, enhancers, termination signals, anti-termination signals and other expression control elements (e.g., sequences to which repressors or inducers bind and/or binding sites for transcriptional and/or translational regulatory polypeptides, for example, in the transcribed mRNA). Such regulatory sequences are described, for example, in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

Regulatory sequences include those which direct constitutive expression of a nucleotide sequence in a microorganism (e.g., constitutive promoters and strong constitutive promoters); those which direct inducible expression of a nucleotide sequence in a microorganism (e.g., inducible promoters, for example, xylose inducible promoters); and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule or recombinant vector of the present invention includes a nucleic acid sequence or gene that encodes at least one bacterial budA or budB gene product operably linked to a promoter or promoter sequence. Advantageous promoters of the present invention include native promoters, surrogate promoters and/or bacteriophage promoters. In one embodiment, a promoter is a promoter associated with a biochemical housekeeping gene or a promoter associated with a ethanologenic pathway. In another embodiment, a promoter is a bacteriophage promoter. Other promoters include tef (the translational elongation factor (TEF) promoter) and pyc (the pyruvate carboxylase (PYC) promoter), which promote high level expression in *Bacillus* (e.g., *Bacillus subtilis*). Additional advantageous promoters, for example, for use in Gram positive microorganisms include, but are not limited to, the amyE promoter or phage SP02 promoters. Additional advantageous promoters, for example, for use in Gram negative microorganisms include, but are not limited to tac, trp, tet, trp-tet, lpp, lac, lpp-lac, lacIq, T7, T5, T3, gal, trc, ara, SP6, γ-$P_R$ or γ-$P_L$.

In another embodiment, a recombinant nucleic acid molecule or recombinant vector of the present invention includes a terminator sequence or terminator sequences (e.g., transcription terminator sequences). Typically, terminator sequences refer to the regulatory sequences that serve to terminate transcription of a gene. Terminator sequences (or tandem transcription terminators) can further serve to stabilize mRNA (e.g., by adding structure to mRNA), for example, against nucleases.

In yet another embodiment, a recombinant nucleic acid molecule or recombinant vector of the present invention includes sequences which allow for detection of the vector containing said sequences (i.e., detectable and/or selectable markers), for example, sequences that overcome auxotrophic mutations, for example, ura3 or ilvE, fluorescent markers, and/or colorimetric markers (e.g., lacZ/β-galactosidase), and/or antibiotic resistance genes (e.g., bla or tet).

It is understood that any one of the budA and budB genes of the invention can be introduced into a vector also comprising one or more ethanologenic genes (e.g., alcohol dehydrogenase (i.e., adh) and pyruvate decarboxylase (pdc) and/or a gene encoding a gene product suitable for fermenting a sugar or degrading a sugar for subsequent fermentation as described for example, in U.S. Pat. Nos. 5,821,093; 5,482,846; 5,424,202; 5,028,539; 5,000,000; 5,487,989, 5,554,520, and 5,162,516. Such two or more genes can be expressed independently using separate regulatory elements (e.g., promoters), common regulatory element(s), native regulatory element(s), or a combination thereof.

V. Methods of Making Recombinant Host Cells Comprising Gene Deletions

As discussed, recombinant host cells in accordance with the invention comprise a mutation in at least one polynucleotide sequence that encodes a protein from a metabolic pathway that leads to the production of products other than ethanol during fermentation of saccharides. Genetic methods for making microorganisms comprising mutations such as deletion mutations are known in the art. Genetic techniques for isolating and manipulating genetic constructs such as PCR-based gene cloning, plasmid constructions and genetic analyses are well established and routine in the art of molecular biology. See, for example, methodology treatises such as Ausubel et al., 1987; Miller, 1992; and Sambrook and Russell, 2001 [24-26]. Methods for producing chromosomal deletions [22] and integrations, including the use of removable antibiotic resistance genes, have also been described [27-29].

Use of such methods to produce an exemplary recombinant host cell having improved ethanologenic properties is further illustrated in Examples 4 and 5, infra, which provide detailed description of PCR-based cloning of genes in the butanediol pathway (budAB) from K. oxytoca, creation of a deletion mutation (knockout) in these genes, and integration of a DNA construct comprising this mutation into the chromosome of K. oxytoca P2, to provide improved strains, designated K. oxytoca B 15, B19 and BW21. The B15 and B19 strains comprise a mutated budAB sequence flanking a FRT-flanked tetracycline gene, i.e., the polynucleotide sequence designated herein as SEQ ID NO:8 (see also Example 5, infra). The BW21 strain comprises the same mutated budAB sequence as the BW15 and BW 19 strains (i.e., a mutated budAB sequence designated herein as SEQ ID NO:5), but lacks the FRT-flanked tetracycline gene, which was removed using FLP recombinase (see also Example 5). The BW21 strain was tested and shown to exhibit superior ethanologenic properties relative to the parent strain, P2.

In yet another aspect, the invention provides a method for producing a recombinant host cell that is optimized for producing ethanol from asaccharide source. The method includes the following steps:

(a) contacting a parent ethanologenic host cell with a selected growth medium and a saccharide source under conditions suitable for ethanol production by the parent cell;

(b) determining the level of ethanol produced from the oligosaccharide source under the selected conditions;

(c) determining the level of at least one and preferably all products other than ethanol produced from the saccharide source, to identify undesirable co-products having increased expression under said conditions;

(d) mutating a polynucleotide sequence of a gene encoding a protein in a metabolic pathway that produces the undesirable co-product, wherein the mutation decreases or eliminates expression of at least one gene product in the metabolic pathway, and increases ethanol production by the mutant cell in the selected medium, as compared to ethanol production by the parent cell in the absence of the mutation, thereby producing a recombinant host cell optimized for ethanol production in the selected medium.

Some embodiments of the method further comprise producing an isolated polynucleotide fragment comprising a mutation of the gene; and introducing the mutated polynucleotide fragment into the parent cell.

Advantageously, the method provides for the construction of recombinant host cells that are custom tailored for optimal ethanol production in particular selected media, and under particular culture conditions. Step (c) of the method, involving identification of co-products that are upregulated in the parent ethanologenic host cell as a result of growth in the particular medium, is used to identify the corresponding metabolic pathways that can be targeted and eliminated by further genetic engineering of the parent cell.

In some embodiments of the method, the cell is optimized for ethanol production in a minimal medium. As discussed, the cost of growth media used in the production of ethanol by recombinant host cells such as bacteria is a very significant factor in the overall production cost. To contain production costs, recent efforts have resulted in the development of "minimal media" comprising minimal amounts of required nutrients from inexpensive sources. (See, for example, Section VI, and Table 2, infra, showing formulations of several minimal media suitable for SSF, including a novel urea-based minimal medium disclosed herein, designated "optimized urea medium," (OUM). One embodiment of the method produces a cell optimized for ethanol production in OUM, e.g., K. oxytoca BW21, comprising deletions in budAB genes that encode butanediol products that are upregulated in this medium at acidic pH, a preferred pH for SSF.

VI. Minimal Media

In another aspect, the invention provides minimal media that support growth and ethanol production by recombinant host cell suitable for degrading a saccharide. A minimal medium in accordance with the invention comprises the following base components:
a defined nitrogen source;
a complex nitrogen source;
a source of phosphate; and
a source of magnesium.

Optionally, sources of metal ions such as $FeCL_2$ and $NiCl_2$ are added in some embodiments of the media, as cofactors that are beneficial for enzymatic activity in certain ethanologenic bacterial strains such as derivatives of *Klebsiella oxytoca*.

In some embodiments of the minimal media in accordance with the invention, the defined nitrogen sources is a urea-like compound. The concentration ranges for urea nitrogen can be from about 0.1 to 100 mM, preferably from about 2.0-20 mM, and more preferably from about 8-12 mM.

Complex nitrogen sources of use in the minimal media can be selected from a variety of sources, including but not limited to corn steep liquor (CSL), yeast autolysate and/or extract, corn processing by-product, soy processing byproduct, and spent fermentation broth, for example from fermentations using microorganisms such as yeast, *streptomycetes, bacilli*, etc.

Some embodiments of the minimal media comprise corn steep liquor (CSL) as a complex nitrogen source. Preferred concentration ranges for CSL in these media are from about 0.1-100 g $L^{-1}$, preferably from about 1-20 g $L^{-1}$ and more preferably from about 5-10 g $L^{-1}$.

It has been determined from studies described herein that concentration ranges of other components, such as total phosphate and magnesium may be less critical to ethanol production. The lowest effective concentration of these components can be determined empirically as described above for urea and CSL. Generally, advantageous concentrations of total phosphate are from about 10-100 mM, and preferably about 10-12 mM. Preferred concentrations of magnesium are in the range of about 0.1-5.0 mM, and more preferably in the range of about 0.25 to 1.0 mM.

In one aspect, the invention provides minimal media that are optimized to support growth and ethanol production by a recombinant host cell suitable for degrading asaccharide. Some embodiments of the media are optimized for selected recombinant host cells and conditions of fermentation. Depending upon the ethanologenic strain to be used, the concentrations of the base components of the minimal media are optimized for cost effectiveness by the determining the minimum concentrations of components consistent with acceptable cell growth and high levels of ethanol production by ethanologenic strains during fermentation of the sugar substrates. (See, for example, studies described in Examples 1-3 and Tables 2 and 3, infra, relating to optimization of minimal urea-based media particularly suitable for use with ethanologenic *K. oxytoca* strains).

Some embodiments of optimized media in accordance with the invention are suitable for methods and conditions used in SFF of lignocellulosic biomass. As discussed, lignocellulose, being inedible by animals, is attractive as an abundant and inexpensive starting material for ethanol production. Abundant sources of lignocellulose are found in waste products including plant residues such as stems, leaves, hulls, husks, cobs and the like, as well as wood, wood chips, wood pulp and waste paper. SSF can be conducted using lignocellulosic biomass as a saccharide source. In the SSF process, soluble products are produced by fungal enzymes (typically cellulases and xylanases) that hydrolyze the lignocellulose. Examples of soluble products released from lignocellulosic products include cellobiose, cellotriose, xylobiose, xylotriose and arabinosides. These soluble sugar products are concurrently converted to ethanol by ethanologenic microorganisms such as recombinant bacteria. Importantly, the fungal enzymes exhibit optimal performance at acidic pH (around pH 5.0), necessitating SSF reactions to be carried out at acidic pH.

As discussed, countering the advantage of lignocellulose as an inexpensive source of biomass for ethanol production is its disadvantage of being poor in nutrients needed to support the ethanologenic bacteria used in the SSF process. The invention addresses this problem by providing in one aspect improved minimal media suitable, for example, for use in SSF with ethanologenic bacteria and lignocellulosic starting materials.

The media are optimized to support maximal growth and ethanol production by ethanologenic strains of bacteria, and to minimize cost by substituting previously used sources of nitrogen, including simple chemical agents such as ammonia and $(NH_4)_2SO_4$ with low levels of urea or urea-like compounds as the sole source of nitrogen. The substitution of these compounds provides a significant cost advantage over use of other nitrogen sources.

A particularly preferred embodiment of a minimal medium in accordance with the invention, designated "optimized urea medium 1" (OUM1) comprises the following components at the indicated concentrations:

| | |
|---|---|
| $NH_2CONH_2$(urea) | 10.0 mM |
| CSL | 10.0 g$L^{-1}$ |
| $KH_2PO_4$ | 10.7 mM |
| $Na_2HPO_4$ | 1.3 mM |
| $CaCl_2$ | 1 mM |
| $MgSO_4$ | 1 mM |
| $FeCl_2$ | 0.074 mM |
| $NiCl_2$ | 0.0068 mM |

For use in fermentation reactions, a source of saccharide is added, for example glucose (e.g., at 90 g $L^{-1}$) or a lignocellulosic source of sugar as described above.

VII. Methods and Systems for Optimized Ethanol Production During Fermentation of a Saccharide Source by Recombinant Host Cells The above-described optimized minimal media of the invention and the recombinant organisms optimized by genetic engineering for maximal ethanol productivity and minimized production of co-products can be advantageously combined in a system for ethanol production Accordingly, in another aspect the invention provides a system for optimized ethanol production from a saccharide source by a recombinant host cell suitable for degrading a saccharide. The system includes the following components:

(a) a selected medium that supports optimal growth and ethanol production by a host cell under the selected conditions;

(b) a source of a saccharide; and (c) a recombinant host cell optimized for ethanol production in the selected medium and conditions, the cell comprising:

a heterologous polynucleotide sequence that codes for an enzyme that converts sugars to ethanol, wherein the cell expresses the heterologous polynucleotide sequence at a sufficient functional level so as to facilitate production of ethanol as a primary fermentation product by the host cell; and a mutation in at least one polynucleotide sequence that codes for a protein in a metabolic pathway in the cell that produces a product other than ethanol from the oligosaccharide source in the selected medium under the selected conditions, wherein the mutation decreases or eliminates expression of the protein, thereby increasing ethanol production the host cell, as compared to ethanol production by the cell when lacking the mutation, thereby optimizing ethanol production.

In embodiments of the system preferred for commercial use, the selected medium is a minimal medium, such as a urea-based minimal medium in accordance with the present invention, as described above.

Any suitable recombinant host cell optimized for ethanol production can be used in the system, as can any suitable saccharide or oligosaccharide source. A preferred inexpensive saccharide source is lignocellulosic material. As discussed, SSF reactions are optimally carried out in the acidic pH range, to optimize efficiency of the fungal enzymes. However, the acidic conditions can have detrimental effects on fermentation by the bacteria, such as increased production of unwanted co-products and concomitant decreased production of ethanol at the preferred pH.

In an optimized system in accordance with the present invention, the detrimental effects of a condition of growth (such as pH), or of the minimal media itself, can be minimized by pairing a particular growth medium with a recombinant bacterium specifically optimized for growth and ethanol production in that medium. For example, if it is known that in a particular medium an undesired metabolic pathway in the host is altered (e.g., upregulated) under the particular conditions of culture, then a system can be designed that pairs that medium with a selected recombinant host cell comprising genetic alterations (e.g., deletion mutations) that target the altered pathway, thereby reducing or eliminating the unwanted product under those conditions. Accordingly, the system is optimized for ethanol production during fermentation reactions in the particular minimal medium.

A preferred embodiment of the optimized system of the invention combines a novel OUM medium as described herein, a recombinant optimized *Klebsiella oxytoca* strain, such as strain BW21, and a lignocellulosic source of sugar. This optimized system for the production of ethanol provides an attractive and inexpensive means of producing ethanol from biomass containing lignocellulose.

A suitable recombinant ethanologenic bacterial strain for fermentation of biomass by SSF is *Klebsiella oxytoca* P2. An exemplary recombinant host cell of the present invention optimized for fermentation of biomass by SSF is an improved ethanologenic strain derived from *Klebsiella oxytoca* P2, designated BW21, that differs from the parent strain in having a deletion mutation that eliminates the co-products of the butanediol pathway (acetoin and 2,3-butanediol). As shown in studies herein, this pathway is specifically upregulated when the P2 cells are grown and used in fermentation studies in a preferred minimal medium (OUM1) containing urea as the defined nitrogen source. In the optimized BW21 cells, expression of these unwanted gene products was eliminated by gene deletion. Assays of ethanol production by BW21 cells demonstrated that these cells possessed superior ability to produce ethanol at acidic pH in the minimal medium than the parent P2 strain, even when grown in rich medium such as Luria broth. Thus, by combining an optimized minimal medium comprising a urea-like compound with a recombinant *Klebsiella* strain optimized for ethanol production in this particular medium, ethanol production was optimized in the system at acidic pH, under conditions suitable for SFF, to levels achievable using more expensive media.

In yet a further aspect, the invention provides kits comprising a recombinant host cell as described above, packaged with instructions for using the recombinant host cell according to the methods or systems of the invention.

Materials and methods generally useful in the practice of the above method are further described below, and in the following Examples.

EXAMPLES

The invention is further illustrated by reference to the following Examples, which should not be construed as limiting.
Materials and Methods:
The following materials and methods were used throughout the Examples below.
1a. Strains and Plasmids:
Table 1 lists the organisms and plasmids used to construct the recombinant microorganisms of the invention.

TABLE 1

Strains and Plasmids

| Strain or | Traits | Source/Reference |
|---|---|---|
| DH5α | lacZΔM15 recA | Bethesda Res Lab |
| *K. oxytoca* M5A1 | prototroph | [5] |
| P2 | pflB::(Zm pdc, adhB) cat | [6] |
| BW15 | M5A1 ΔbudAB::FRT-tet-FRT | See text |
| BW19 | P2 transductant from BW15, ΔbudAB::FRT-tet-FRT | See text |
| BW21 | BW19 Tc$^s$, ΔbudAB::FRT | See text |
| pCR2.1-TOPO | TOPO T/A PCR cloning vector bla kan | Invitrogen |
| pLOI2065 | FRT-tet-FRT | [20] |
| pFT-K | FLP Recombinase kan | [21] |
| pKD46 | Red recombinase, bla | [22] |
| pHP45W | aac | [23] |
| pLOI2745 | temperature conditional vector, pSC101$^{rs}$, kan | See text |
| pLOI3301 | pCR2.1 budAB' | See text |
| pLOI3310 | pLOI3301 budA'FRT-tet-FRT 'budB' | See text |
| pLOI3313 | pLOI2745 budA'FRT-tet-FRT 'budB' | See text |
| pLOI3421 | 1.8 kbp SmaI frag. containing aac from pHP45W XmnI | See text |

1b. Growth Media and Conditions

Ethanologenic strains were maintained on Luria agar [24] containing 2% glucose and chloramphenicol (40 or 600 mg L$^{-1}$ on alternate days) under argon. Other strains were maintained on Luria agar plates lacking added sugar with appropriate antibiotics. Unless otherwise noted, ampicillin (50 mg L$^{-1}$), kanamycin (50 mg L$^{-1}$), apramycin (50 mg L$^{-1}$), and tetracycline (12.5 mg L$^{-1}$) were used for selection. Strains harboring plasmids with temperature conditional replicons were grown at 30° C. All other strains were maintained at 37° C., except where noted. Plasmid preparations were stored at −20° C. Stock cultures were stored in glycerol at −75° C.

1c. Genetic Methods:

Standard methods were used for PCR-based gene cloning, plasmid constructions, and genetic analyses [24-26]. Methods for integration, chromosomal deletions, integration, and the use of removable antibiotic resistance genes were used as previously described [22, 27-29]. *E. coli* DH5α was used for constructions.

1d. Deletion of budA and budB Genes.

A DNA fragment containing α-acetolactate decarboxylase (budA) and the 5' end of α-acetolactate synthase (budB) was amplified by PCR using genomic DNA from *K. oxytoca* as a template and Taq PCR Master Mix (Qiagen). After an initial denaturation at 94° C. for 3 min, DNA was amplified for 30 cycles (denaturation at 94° for 30 s, annealing at 55° C. for 30 s and extension at 72° C. for 70 s). A final elongation step at 72° C. for 10 min was also included.

The budAB' DNA fragment was amplified using the following primers:
forward primer: 5'GCTGAATCGGGTCAACATTT-3' (SEQ ID NO:1)
reverse primer: 5'-TTTCGGTTTGTCCAGGTAGT-3' (SEQ ID NO:2)
and cloned into pCR2.1-TOPO. This fragment, designated pLOI3301, was sequenced and has been deposited in GenBank (Accession No. AY722056).

For preparation of a DNA fragment containing deletions in budAB, a cloning/deletion strategy was used in which the central region of the budA and budB genes was deleted and replaced with a tetracycline gene flanked by two FRT sites. The resulting construct, carrying budA and budB deletions (budA' FRT-tet-FRT 'budB) (SEQ ID NO: 8) was integrated into a temperature conditional vector, pSC101$^{rs}$ and used to stably transform ethanologic bacteria.

FIG. 1 is a schematic diagram showing steps in the preparation of exemplary constructs (pLOI3301, pLOI3310 and pLOI3313) comprising deletion mutations in budAB that result in elimination of the butanediol products of fermentation when introduced into ethanologenic bacteria. Further detailed description of FIG. 1 and of the methods used to produce these plasmids is found infra, in particular in Example 4.

1e. Production of Strain BW21 from *Klebsiella oxytoca* P2.

DNA constructs comprising deletion mutations in budA and budB, prepared as described in 1d above, were used to produce recombinant bacteria transformed with these constructs. See, for instance, Example 5 describing transformation of ethanologenic strain *K. oxytoca* M5A1. Bacteriophage P1 (an *E. coli* phage) was then used to transduce the budAB chromosomal deletion constructed in *K. oxytoca* M5A1 into strain P2 to produce strain BW21.

1f. Assessment of Butanediol Pathway By Screening for Absence of Acetoin Product of BudA:

Strains were screened for acetoin production using a modification of the Vogues-Proskaur (VP) agar method described by Blomqvist, et al. [35] that used microtiter plates instead of petri plates, increasing the sensitivity by limiting diffusion of the colored product. Each well was filled with 1 ml of the medium (per liter: 2.5 g Difco Bactopeptone, 1.0 g Difco yeast extract, 10 g glucose, 1.0 g sodium pyruvate, and 25 g agar), and inoculated. After 24 hours, 200 µL of a 5% α-napthol solution in 2.5 N NaOH was added to each well. Color development was monitored for 1 h at room temperature. The absence of red color confirmed the lack of acetoin (product of BudA activity). Additional confirmation was provided by HPLC analysis of fermentation products.

2a. Minimal Media for Ethanologenic Bacteria:

Components of media, both previously known and as developed herein (optimized urea medium 1, OUM1), are summarized in Table 2.

TABLE 2

Composition of Media (excluding fermentable sugar)

| Component[a] | LB[b] | M9(+Fe)[c] | U-M9(+Fe)[d] | 0.5% CSL + M[e] | U-0.5% CSL + M[f] | OUM1[g] |
|---|---|---|---|---|---|---|
| Media Composition (mM) | | | | | | |
| KH$_2$PO$_4$ | | 22 | 22 | 7.4 | 7.4 | 10.7 |
| K$_2$HPO$_4$ | | | | 2.9 | 2.9 | |
| Na$_2$HPO$_4$ | | 42 | 42 | | | 1.3 |
| Total PO$_4$ | | 64 | 64 | 10.3 | 10.3 | 12 |
| NaCl | 85.6 | 9 | 9 | | | |
| CaCl$_2$ | | 0.1 | 0.1 | 1 | 1 | 1 |
| MgSO$_4$ | | 1 | 1 | 2 | 2 | 1 |
| FeCl$_3$ | | 0.074 | 0.074 | 0.074 | 0.074 | 0.074 |
| NiCl$_2$ | | | 0.0068 | | 0.0068 | 0.0068 |
| NH$_4$Cl | | 19 | | | | |
| (NH$_4$)$_2$SO$_4$ | | | | 23.5 | | |
| NH$_2$CONH$_2$ | | | 10 | | 23.5 | 10 |
| Total Nitrogen[h] | | 19 | 20 | 47 | 47 | 20 |
| Tryptone (gL$^{-1}$) | 10 | | | | | |
| Yeast extract | 5 | | | | | |
| CSL (gL$^{-1}$) | | | | 10 | 10 | 10 |

[a]Degree of hydration is omitted for simplicity.
[b]Luria Broth
[c]M9 medium (30).
[d]M9 with NH$_4$Cl replaced with equivalent urea nitrogen.
[e]0.5% CSL + M (32).
[f]0.5% CSL + M media except that (NH$_4$)$_2$SO$_4$ was replaced with equivalent urea nitrogen.
[g]OUM1, optimized urea media number 1.
[h]Total mmoles of available nitrogen.

Each medium tested in fermentation reactions with either 50 g L$^{-1}$ (278 mM) glucose or 90 g L$^{-1}$ (500 mM) glucose. Components were purchased from either the Fisher Scientific Company or the Sigma Chemical Company. Inorganic salts were reagent grade. Urea was technical grade. M9 medium was prepared as previously described [30] and further supplemented with 0.07 mM FeCl$_3$ to ensure adequate levels for iron-requiring *Z. mobilis* alcohol dehydrogenase [31]. Corn steep liquor (CSL) medium for ethanologenic *E. coli*, (0.5% CSL+M), has been previously described [32]. Both M9 and 0.5% CSL+M media were used as starting points to optimize a medium for ethanologenic derivatives of *K. oxytoca* M5A1. When urea was used as the nitrogen source, 0.007 mM NiCl$_2$ was added for urease activity. CSL levels are expressed on a dry weight basis. Stock solutions of CSL were prepared and sterilized as previously described [33].

*K. oxytoca* P2 was used in all media optimization studies. Isolated colonies from freshly grown plates (24 h) were resuspended in 1 ml of deionized $H_2O$ and used to inoculate 125 ml flasks (~50 μL inoculum) containing 75 ml of medium (50 g $L^{-1}$ glucose). Growth and ethanol production were monitored after 24 and 48 hours.

2b. Fermentation Conditions:

Seed cultures (150 ml in 250 ml flasks) were grown for 16 h at 35° C. (120 rpm) in media containing 50 g $L^{-1}$ glucose. Cells were harvested by centrifugation (5000×g, 5 min) and used as inocula to provide an initial concentration of 33 mg $L^{-1}$ dry cell weight ($OD_{550}$=0.1). Respective media used for fermentations were also used for seed growth but with a lower concentration of glucose (50 g $L^{-1}$). Fermentation vessels were previously described [34] and contained an initial volume of 350 ml (90 g $L^{-1}$ glucose). Cultures were incubated at 35° C. (150 rpm). Broth was maintained at pH 5.2 (except where noted) by the automatic addition of 2N KOH.

2c. Analytical Methods:

Cell mass was estimated by determining $OD_{550nm}$ with a Bausch & Lomb Spectronic 70 spectrophotometer. With this instrument, 1 $OD_{550nm}$ corresponds to a cell density of 0.33 mg (dry wt.) $L^{-1}$. Measurements of cell density for *K. oxytoca* have a large error due to the clumping nature of the cells. Ethanol was measured by gas chromatography using a Varian model 3400× as previously described [11]. Other fermentation products were determined by high-performance liquid chromatography (HPLC) using a Hewlett-Packard model 1090 series II chromatograph and a Bio-Rad Aminex 87H ion partition column (45° C.; 4 mM $H_2SO_4$; 0.4 ml $min^{-1}$; 10 μL injection volume) with dual detectors (refractive index and $UV_{210nm}$) [33]. Carbon balances were calculated as previously described [29, 36]. When LB was used as the fermentation medium, cell mass was assumed to be produced exclusively from the complex media components and was not included in calculations of carbon balance.

Example 1

Minimal Media for Growth and Ethanol Production by *K. oxytoca* P2

This example describes the development of a novel minimal medium (OUM1) comprising urea as the sole source of nitrogen, optimized for growth and ethanol production by recombinant ethanologenic bacteria such as *Klebsiella* strains. The new medium was developed and optimized using strain *K. oxytoca* P2, by comparing its growth and ethanol production capacity with that of several known media.

Previously described media used for comparative purposes were the following:

Luria broth (LB) (Ausubel et al., 1989);

M9 medium (+Fe) (Neidhardt et al., 1974);

U-M9 (+Fe), in which $NH_4Cl$ is replaced with equivalent nitrogen from urea;

0.5% corn steep liquor, CSL+M (Martinez et al., 1999);

U-0.5% CSL+M, in which $(NH4)_2SO_4$ is replaced with equivalent nitrogen from urea. The new media is referred to herein as "optimized urea medium number 1" (OUM1). The formulations of each of the above media are listed in Table 2, supra.

Figure 2A:
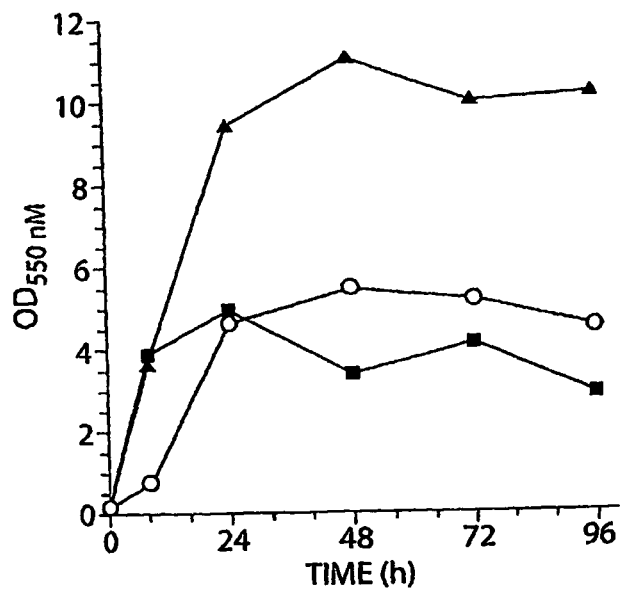
FIGS. 2A-2D are four graphs showing fermentation by recombinant strains of ethanologenic microorganism *K. oxytoca* P2 in various minimal media and Luria broth containing 90 g L$^{-1}$ glucose, according to an embodiment of the invention.
Figure 2B:
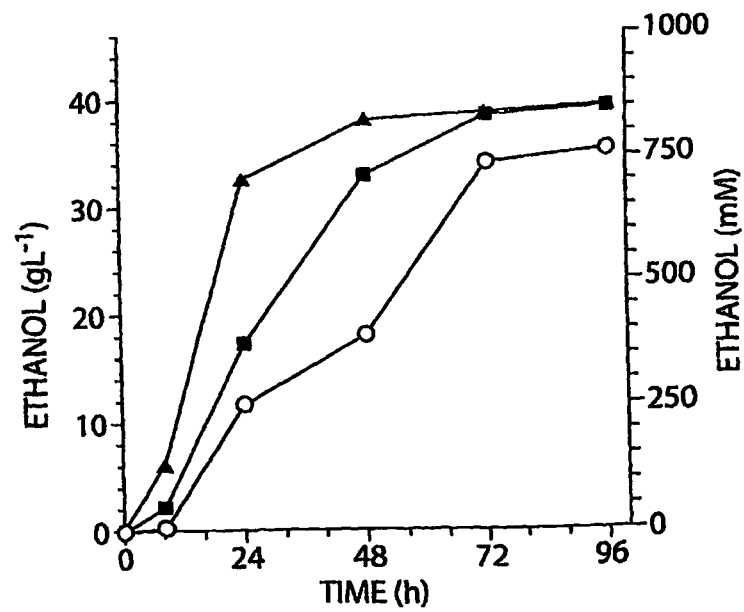

In initial studies to develop the optimized media, cell growth and ethanol production capacity were compared in *K. oxytoca* P2 tested at pH 5.2 in M9 (+Fe) and 0.5% CSL+M media, the latter having ammonia as the sole nitrogen source. LB medium at pH 5.2 was included as a control to provide a benchmark for performance. Referring to FIGS. 2A and 2B, as expected [32], LB medium supported the highest cell yield (FIG. 2A) and the most rapid ethanol production (FIG. 2B). Equivalent levels of ethanol were produced in 0.5% CSL+M and LB (FIG. 2B).

Table 3 shows, inter alia, the effect of replacing ammonia with urea on ethanol production and yield in both M9 and CSL+M media. As can be seen, this change resulted in a small decrease in ethanol production (71% vs. 76% yield for M9; 78% vs. 83% for CSL+M). As is also shown in Table 3, in general, ethanol productivity and yields increased with the richness of the media (LB>0.5% CSL+M>M9+Fe), regardless of nitrogen source.

TABLE 3

Production of Ethanol and Co-products in Various Media (90 $gL^{-1}$ glucose, 72 h).[a]

| Strain | Medium | pH | n | Ethanol (mM) | Ethanol Yield[b](%) | Formate (mM) | Lactate (mM) | Succinate (mM) | Acetate (mM) | Acetoin + 2,3 Butanediol (mM) | Carbon Recovery[c] (% total) |
|---|---|---|---|---|---|---|---|---|---|---|---|
| P2 | LB | 5.2 | 2 | 848 | 85 | <1 | 25 | 8 | <1 | 31 | 110 |
| P2 | M9 + $NH_4$ | 5.2 | 2 | 761 | 76 | <1 | 22 | 18 | <1 | 24 | 96 |
| P2 | 0.5% CSL + $NH_4$ | 5.2 | 2 | 831 | 83 | <1 | 13 | 8 | <1 | 23 | 101 |
| P2 | U-M9 | 5.2 | 2 | 708 | 71 | <1 | 33 | 12 | <1 | 18 | 89 |
| P2 | U-0.5% CSL + M | 5.2 | 2 | 776 | 78 | <1 | 15 | 20 | <1 | 19 | 95 |
| P2 | OUM1 | 5.2 | 10 | 825(65) | 83 | <1 | 10(5) | 13(5) | 9(3) | 72(20) | 101(6) |
| BW21 | OUM1 | 5.2 | 4 | 926(17) | 93 | <1 | 4(1) | 13(3) | 5(1) | 2(1) | 100(2) |
| P2 | LB | 6.0 | 2 | 998 | 100 | 11 | 37 | 12 | 25 | 39 | 111 |
| P2 | LB | 6.8 | 2 | 979 | 98 | 66 | 28 | 11 | 34 | 38 | 112 |
| P2 | OUM1 | 6.8 | 2 | 806 | 81 | 44 | 30 | 17 | 47 | 16 | 96 |

[a]Values are corrected for dilution by added base. Standard deviations are shown in parentheses for n values of 3 or more values.
[b]Percentage of theoretical yield based on total glucose (90 $gL^{-1}$).
[c]Includes unmetabolized glucose remaining after 72 hours.

Example 2

Optimized Minimal Media Comprising Urea as the Defined Nitrogen Source

This example describes a procedure for developing optimized minimal media comprising urea for use with ethanologenic bacteria, and provides the formulation of an embodiment of such a medium designated "OUM1."

Figure 2C:
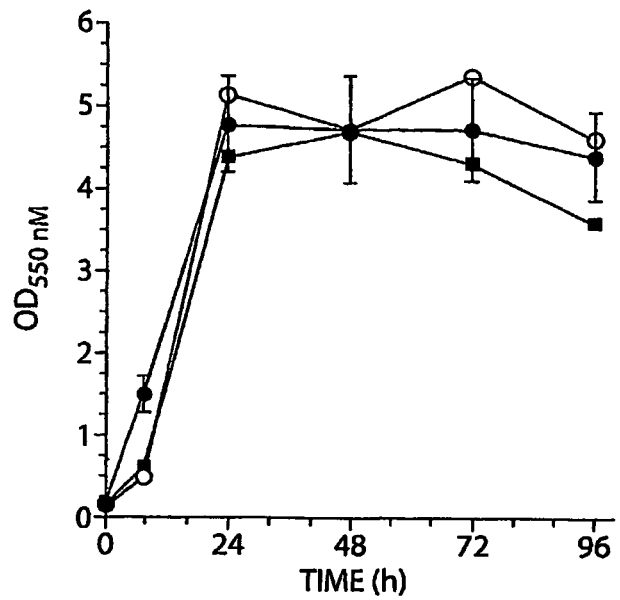
Figure 2D:
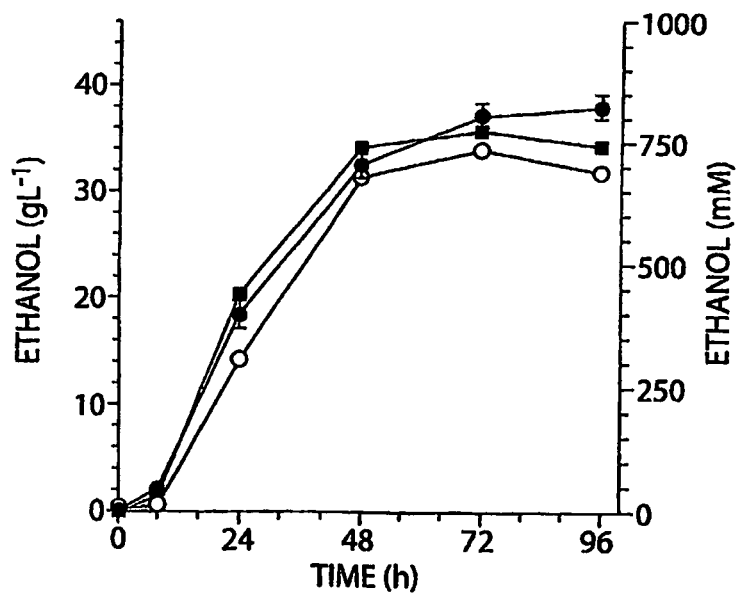

A urea-based medium, designated OUM1 (having urea as the only defined nitrogen source), was tested in pH-controlled fermentations at pH 5.2 with 90 g $L^{-1}$ glucose, using methods as described above. Ethanol production in this medium was slightly superior to urea-containing formulations of M9 (+Fe)

and CSL+M media, confirming that higher levels of nitrogen, phosphate, and CSL are not necessary (FIGS. 2C and 2D).

Results of cell growth studies showed that maximum cell densities were quite similar in M9 (+Fe) and 0.5% CSL+M media (FIG. 2A), and in OUM1 medium (FIG. 2C), suggesting that the lower levels of nitrogen (19.0 mM in M9) and phosphate (10.3 mM in 0.5% CSL+M) in these respective media are adequate.

Figure 3A:
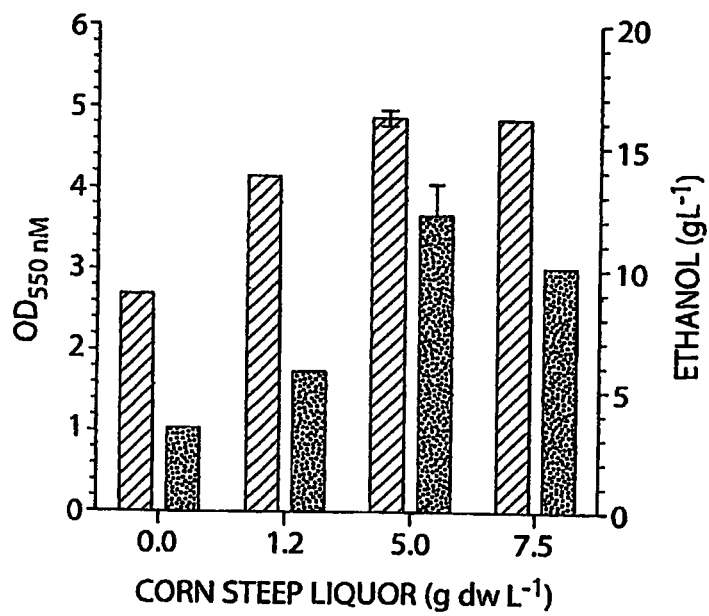
FIGS. 3A and 3B are two graphs showing aspects of fermentation of glucose to ethanol by K. oxytoca P2 in a urea-based minimal medium (OUM1) optimized for K. oxytoca P2 strains, according to an embodiment of the invention. Data depict growth at 48 hr in flask cultures (hatched bars, $OD_{550}$) and ethanol production (solid bars) in media comprising varying concentrations of corn steep liquor (FIG. 3A) and urea (FIG. 3B). Standard errors are included for data with n≥3.
Figure 3B:
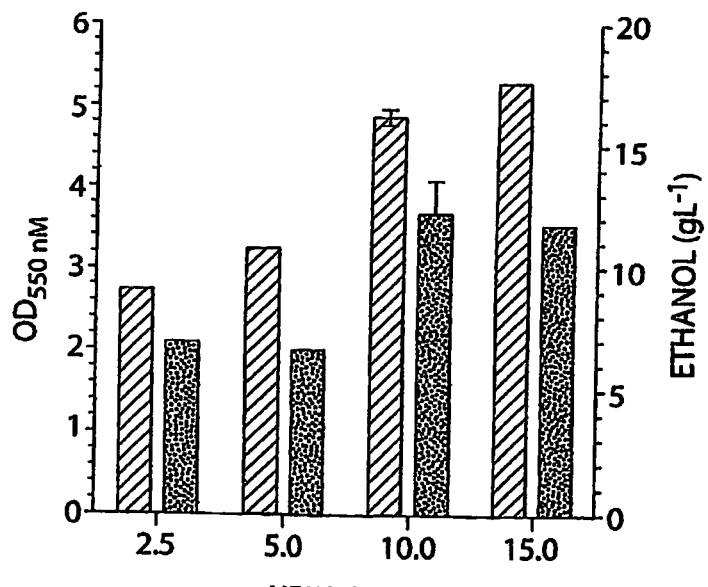

Based on the compositions of M9 (+Fe) and 0.5% CSL+M, flask experiments were designed to evaluate different levels of nutrients in OUM1 medium: phosphate (12-72 mM), magnesium (0.25-1.0 mM), CSL (0-15 g $L^{-1}$), and urea nitrogen (2.5-15 mM). Results of experiments varying the concentrations of corn steep liquor and urea are shown in FIGS. 3A and 3B, respectively. The data showed that over the stated ranges, only CSL and urea had clear optima, i.e., 10 g $L^{-1}$ and 10 mM, respectively. Similar concentrations of ethanol (13.9±1.3 g $L^{-1}$) were produced after 48 h with all levels of other components. Although it is possible that lower concentrations may be adequate, 12 mM $PO_4^{-3}$, 1 mM $MgSO_4$, and 1 mM $CaCl_2$ were selected for the optimized urea medium (OUM1). (See Table 2 for complete formulation of OUM1 medium).

Example 3

Effect of Acidic pH on Ethanol Titers and Production of Co-products of Fermentation As discussed above, for certain types of fermentation reactions, for example those in which fermentable sugars are derived from lignocellulosic feedstocks, it is desirable to conduct the reactions at acidic pH, as this is the range in which fungal hydrolases and cellulases exhibit optimal performance. This example describes the effect of pH on production of ethanol and byproducts of fermentation by ethanologenic bacterial strain P2 grown in various media, including newly developed medium OUM1.

Referring again to Table 3, results of ethanol production from glucose by strain P2 grown in OUM1 medium is compared with results for these cells grown in previously described media. As can be seen in Table 3, ethanol titers with OUM1 media were generally equivalent to those obtained with LB media at pH 5.2.

It was noted in these studies, however, that ethanol titers with all media were lower at pH 5.2 than previously reported in rich media, e.g., Luria broth (LB) at more neutral pH [5, 6]. The detrimental effect of low pH on ethanol production was confirmed for fermentations with both LB and OUM1 media. As shown in Table 3, strain P2 in LB media produced ethanol yields of 100% and 98%, respectively, at pH 6.0 and 6.8, whereas yields were reduced to 85% at pH 5.2.

In the fermentation experiments shown in Table 3, the levels were also determined for several undesired co-products (in addition to ethanol) made from the glucose substrate, i.e., formate, lactate, succinate, acetate, acetoin and 2,3-butanediol. Although co-products were made by strain P2 in all media at pH 5.2, it was seen that an unexpectedly high level (72 mM) of products from the 2,3-butanediol pathway was produced with OUM1 medium at this pH (Table 3). In both LB medium and OUM1 medium, fermentations at pH 5.2 contained a higher proportion of neutral co-products (acetoin and 2,3-butanediol) than at pH 6.8. More particularly, in OUM1 medium, the levels of neutral co-products were 4.5 fold higher at pH 5.2 than at pH 6.8. In contrast, in OUM1 medium at pH 6.8, butanediol acetoin levels were reduced (16 mM vs. 72 mM), and acetate and formate levels were increased at pH 6.8 (47 mM vs. 9 mM, and 44 mM vs. <1 mM, respectively). Unlike the results in OUM1 medium, in LB medium, the levels of neutral co-products remained relatively constant at pH 5.2 and 6.8 (31 mM vs. 38 mM) while acidic co-products declined (Table 3).

Without intending to be bound by theory, it is believed that the increased formation by strain P2 of neutral co-products from the 2,3-butanediol pathway may be related both to the composition of the OUM1 medium and to the low pH. The findings appear to be consistent with reported activities of the corresponding enzymes in native strains of *K. oxytoca*. For example, enzyme activities concerned with the production of co-products of the 2,3-butanediol pathway are known to increase in response to low pH [35, 37, 38]. At more neutral pH, acidogenic activities such as pyruvate formate-lyase, acetate kinase, and lactate dehydrogenase produce more acidic products [39].

Example 4

Constructs for Deletion of budAB Operon in Ethanologenic Bacteria

This example describes the isolation of a putative full-length cDNA sequence for the budA gene, and a partial cDNA sequence for the budB gene, derived from bacteria (*Klebsiella oxytoca*), and construction of DNA fragments in which these genes in the butanediol pathway have been disrupted. Following introduction into bacterial cells, these constructs are useful for eliminating the production of unwanted 2,3-butanediol and acetoin co-products during fermentation of saccharides by the cells.

The budA and budB genes are contiguous in the *K. oxytoca* genome and are designated together as budAB. The two genes encode, respectively, two enzymes involved in the production of 2,3-butanediol and acetoin, i.e., α-acetolactate decarboxylase and α-acetolactate synthase. In this Example, deletions in the budAB genes of *K. oxytoca* M5A1 were constructed and transduced into *K. oxytoca* strain P2, to produce strain BW21. In general, the methods used to construct the deletion mutation strains such as BW21 are described in Materials and Methods, sections Ia-c, supra. The plasmids and strains used to construct the new strain with budAB deletions are listed in Table 1, supra.

The budAB genes have not been previously described in *K. oxytoca*. Homologous genes are known, however, from two related organisms, i.e., *Enterobacter aerogenes* and *Roultella terrigena* (formerly *Klebsiella terrigena*; [35, 37]). Based on these sequences and the partial (unannotated) genome of *K. pneumoniae* [40], primers as described above (SEQ ID NOS: 1 and 2) were designed for PCR amplification of a DNA fragment containing budAB'.

FIG. 1 is a schematic diagram showing the Bud operon and the steps in the construction of plasmids used to delete the 2,3-butanediol fermentation pathway involving this operon in *K. oxytoca*. The inset (FIG. 1A) is a diagrammatic representation of the operon. As indicated in FIG. 1A, expression of this operon is increased by low pH, and positively regulated by BudR and Fnr.

As described in the Methods above, a DNA fragment containing the putative full length coding sequence of α-acetolactate decarboxylase (budA) (SEQ ID NO. 3) and a partial coding sequence comprising the 5' end of α-acetolactate synthase (budB) (SEQ ID NO:4) was amplified by PCR using genomic DNA from *K. oxytoca* as a template. (The predicted amino acid sequences of the polypeptides encoded by SEQ ID NOS: 3 and 4 are set forth in SEQ ID NOS: 6 and 7, respectively.) The diagram in the upper left of FIG. 1B shows the portion of the budA and budB genes of *K. oxytoca* amplified by the indicated PCR primers (SEQ ID NOS: 1 and 2).

Figure 1B:
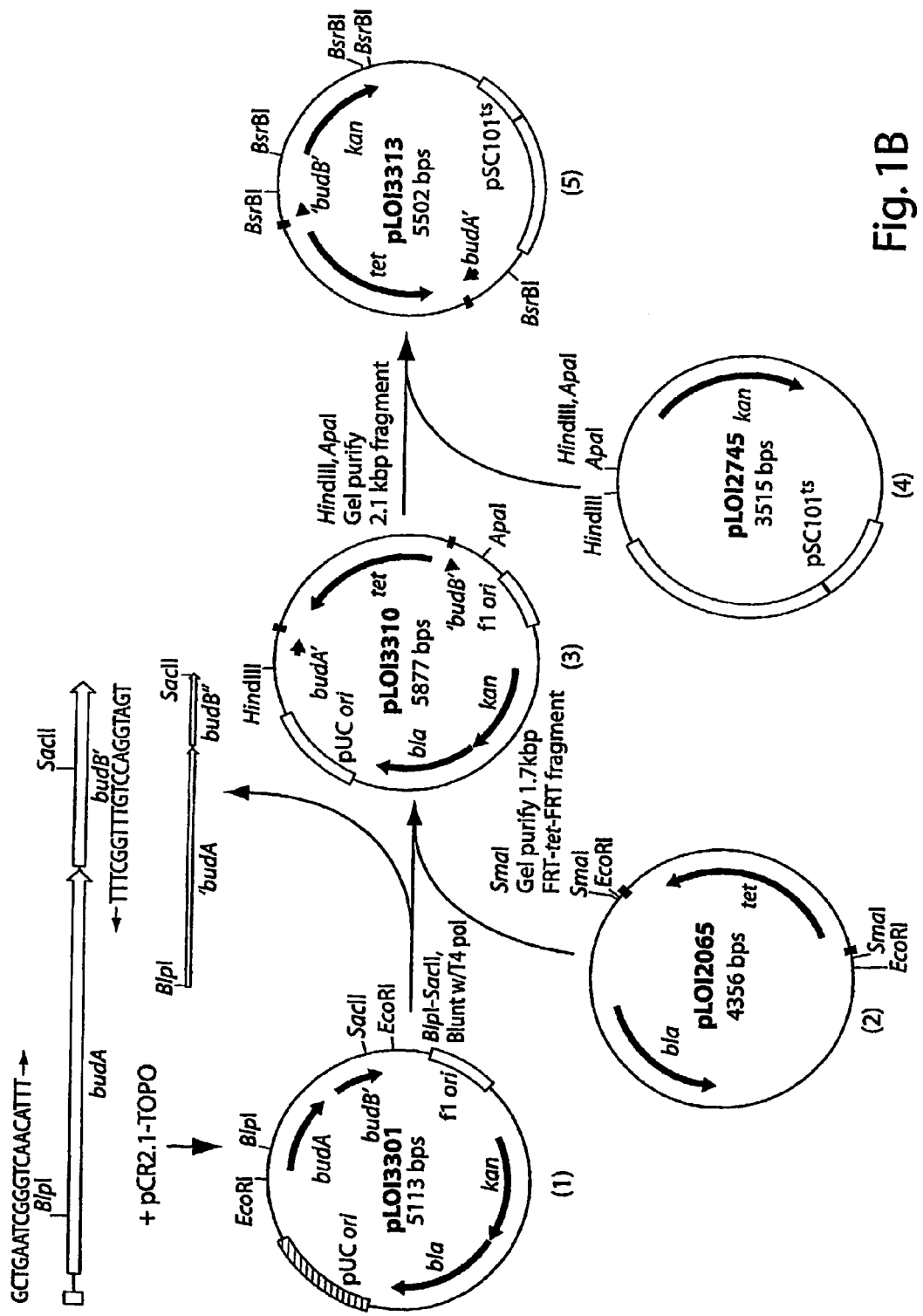
FIG. 1B (upper left) shows PCR primers used to clone budAB'. In the lower portion of the drawing, plasmids (e.g., pLOI3301) used in the construction of a recombinant ethanologenic microorganism optimized for ethanol production in a minimal medium, according to an embodiment of the invention, are shown diagrammatically and indicated by numbers.

Referring to the lower portion of FIG. 1B, the amplified DNA fragment comprising budAB was cloned into PCR cloning vector pCR2.1-TOPO (described in Table 1), to produce pLOI301 (pCR2.1 budAB'; indicated by (1) in FIG. 1B).

To eliminate the budAB gene product, a large central region of the budAB' fragment was deleted and replaced with a tet gene flanked by two FRT (Flp recombinase Recognition Target) sites, to produce pLOI3310 (budA'-FRT-tet-FRT-'budB'; FIG. 1B, (3)). A nucleic acid construct comprising the truncated budA and budB sequences and the intervening FRT-flanked tetracycline gene (budA'-FRT-tet-FRT-'budB)' is designated herein as SEQ ID NO:8. Deletion of the central portion of the budAB sequence, and replacement with the tet-containing construct was accomplished by standard techniques known in the art using pLOI2065 (FIG. 1, (2)) which contains the tet gene flanked by two FRT sequences (Underwood et al., 2002; see also Table 1). Flanking FRT sites were included to facilitate marker removal after chromosomal integration [20, 21, 27].

To minimize background during subsequent integration, the 2.1 kbp HindIII-ApaI fragment comprising budA'-FRT-tet-FRT-'budB' from pLOI3310 was ligated into corresponding sites of pLOI2745 (FIG. 1, (4)). This vector contains a temperature-conditional pSC101 replicon (see Table 1 for further description). The resulting 5502 bp plasmid was designated (pLOI3313) (pLOI2745 (budA'-FRT-tet-FRT-'budB') (FIG. 1B, (5)).

Example 5

Production of Recombinant Ethanologenic *Klebsiella* Bacterial Strains with budAB Deletions As demonstrated in Example 3 and Table 3 above, during fermentation reactions, recombinant ethanologenic strain *K. oxytoca* P2 exhibits reduced ethanol productivity and increased production of co-products of the butanediol pathway when grown at acidic pH in OUM1 fermentation medium. As discussed, the budAB genes encode two enzymes involved in the production of 2,3-butanediol and acetoin, i.e., α-acetolactate decarboxylase and α-acetolactate synthase, respectively. This Example describes the production of a new ethanologenic strain of *K. oxytoca*, strain BW21, derived from strain P2, that comprises deletions in the budAB genes that result in elimination of expression of the budAB gene products in the mutant cells.

For integration of the budA'-FRT-tet-FRT-'budB' fragment into *Klebsiella* strains useful for ethanol production, the pLOI3313 plasmid, described in Example 4 above, was linearized and used as a template for PCR amplification. The PCR product containing the budAB deletion was integrated into strain *K. oxytoca* strain M5A1 by electroporation in the presence of Red recombinase (pLOI3421; see Table 1).

To verify functional deletion of the budAB gene products, ten clones were grown in optimized urea medium (OUM1; see Table 2 supra) containing 5% glucose, and screened for the presence or absence of acetoin and 2,3-butanediol as described in Methods, 1f. Absence of detectable levels of these products confirmed deletion of the budAB pathway in the successfully transformed cells, also termed "deletion clones." Deletion of budAB in the clones was also confirmed by PCR analysis.

For construction of ethanologenic strains of *K. oxytoca* (such as P2) having deletions in the butanediol pathway, one deletion clone of *K. oxytoca* strain M5A1 (designated BW 15) was selected and used as a donor for transduction into *K. oxytoca* P2 using bacteriophage P1, as described above. Ten resulting transductants were screened for acetoin and butanediol production as described. One deletion clone was selected for further study, and designated strain BW19. The FRT-flanked tet gene was subsequently removed by standard procedures using FLP recombinase (pFT-K). The resultant strain, having the budAB deletion but lacking FRT-flanked tet was designated *K. oxytoca* strain BW21. An isolated nucleic acid fragment comprising the truncated budA and budB sequences that remain in the cells after removal of the FRT-flanked tet gene is designated herein as SEQ ID NO:5.

Example 6

Deletion of budAB Increases Ethanol Yields by Ethanologenic Bacteria

This example describes the improved ethanologenic properties and the decreased production of co-products of fermentation of glucose by the newly developed ethanologenic strain *K. oxytoca* BW21 (described in Example 5), in comparison with the parent strain *K. oxytoca* P2.

Referring again to Table 3, a comparison is now made of the effect of budAB deletion (strain BW21 vs. parent strain P2) on production of ethanol and co-products of fermentation by cells grown in OUM1 (with 90 g $L^{-1}$ glucose).

As shown in the table and previously discussed, in fermentations by parent strain P2 carried out at pH 5.2, unwanted co-products (acetoin+2,3-butanediol) from the butanediol pathway (2 mol pyruvate per mol product) were produced from approximately 14% of the glucose available for ethanol production. In striking contrast, deletion of the genes encoding acetolactate synthase and acetolactate decarboxylase in strain BW21 essentially eliminated both of these co-products (Table 3). Lactate and acetate levels were also lower in strain BW21 than in parent strain P2.

Figure 4A:
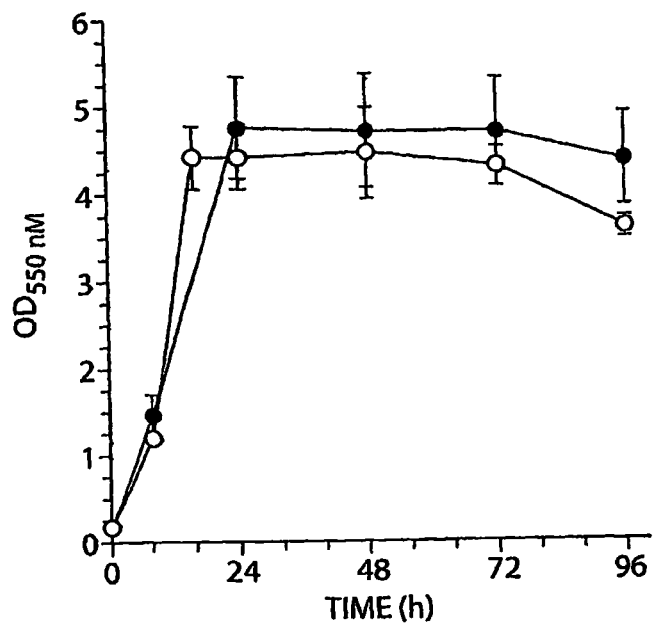
FIGS. 4A and 4B are two graphs showing effects of deletion of budAB gene products on growth and ethanol production by ethanologenic strains of K. oxytoca (90 g L$^{-1}$ glucose).
Figure 4B:
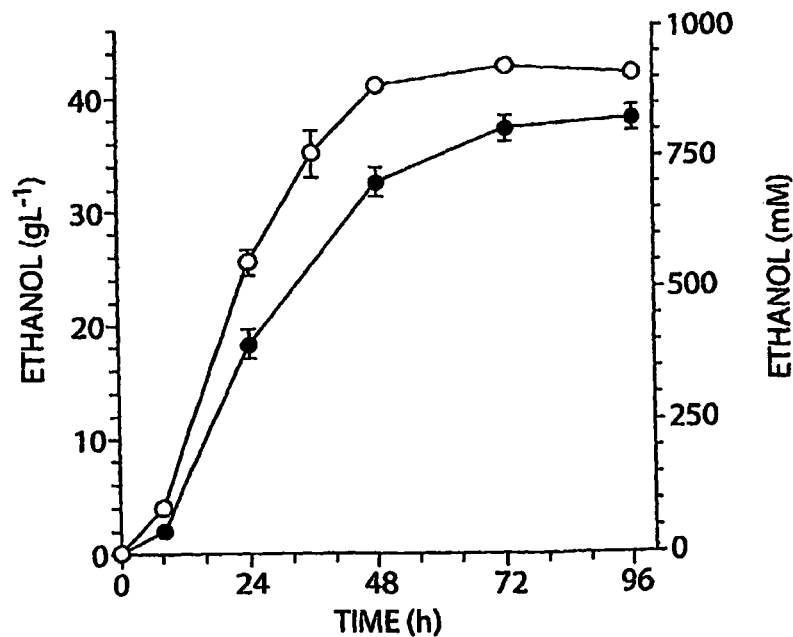

In OUM1 medium at pH 5.2, the decrease in co-products by strain BW21 was accompanied by a 12% increase in ethanol titer and yield in comparison to strain P2 (See Table 3 and FIG. 4.) The graphs in FIG. 4 show a comparison of cell growth (4A) and ethanol production (4B) by *K. oxytoca* strains BW21 and P2 in OUM1 medium. Although the growth rates of BW21 and P2 were essentially the same, ethanol production was consistently higher in strain BW21.

Figure 5:
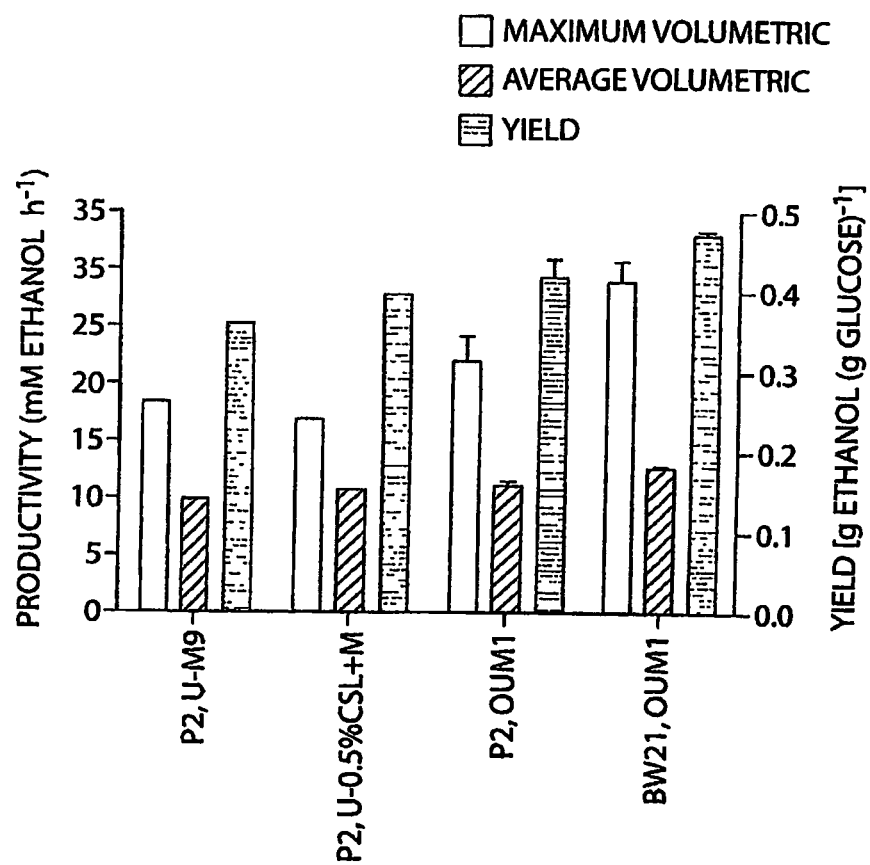
FIG. 5 is a graph showing comparison of ethanol yield and productivity by recombinant bacteria (parent strain P2, and mutant strain BW21 with budAB deletion), according to an embodiment of the invention. Ethanol production by the deletion strain exceeds that of the parent strain.

FIG. 5 shows a comparison of the ethanol yield (expressed in grams, per gram of glucose) and ethanol productivity (expressed as maximum and average volumetric rates of ethanol production, in mM ethanol per hour) for parent P2 strain grown in three urea-containing media, i.e., U-M9, U-0.5% CSL+M and OUM1 (refer to Table 2 for media formulations), and for strain BW21 with budAB deletions, grown in OUM1 medium. Average productivities are calculated for the initial 72 h. Ethanol yields are calculated after 72 h. Maximal volumetric productivity occurs early in fermentation, between 8 h and 24 h.

Importantly, as can be seen in FIG. 5, both ethanol yield and productivity were consistently higher for strain BW21 grown in OUM1 medium than for the parent P2 strain grown in any of the media tested.

Example 7

Economical Production of Ethanol by Recombinant Bacteria Lacking budAB Genes Grown in OUM1 Medium As discussed above, the product yields and costs associated with production materials such as bacterial culture media are important factors in the economics of commodity chemicals such as ethanol. *K. oxytoca* is an advantageous choice as an ethanologenic microorganism because this bacterium has the native ability to use urea as a nitrogen source. On an equivalent nitrogen basis, urea is typically sold for about half the cost of ammonium salts. The use of urea as a nitrogen source has further additional benefits. Unlike the metabolism of ammonium salts, the metabolism of urea does not contribute to the acidification of the media [41] and thus reduces the amount of base required for pH control.

The new media described herein, designated OUM1, offers further potential savings from the low concentrations of other salts and corn steep liquor. On a weight basis, OUM1 medium consists of 0.5% CSL, 0.06% urea, and 0.2% inorganic salts, plus fermentable sugar. The low pH used in these fermentations is particularly appropriate for lignocellulosic feedstocks because fungal cellulases and xylanases typically exhibit optima around pH 5 [42].

As recognized herein, despite these advantages of low pH for SSF, a disadvantage to conducting fermentation reactions at acidic pH is that the pathway for butanediol (and acetoin) production in the ethanologenic bacteria is activated by low pH [43], leading to an increase in co-products and decline in ethanol yield. However, as demonstrated herein, this problem can be successfully overcome by constructing improved recombinant ethanologenic bacterial strains having deletions in the two genes uniquely involved in this pathway (budAB). As shown above, elimination of the butanediol reaction products by deletion of these genes resulted in an improved ethanologenic *Klebsiella* strain (exemplified by strain BW21) that attained 12% higher ethanol yields than the parent strain P2. Most significantly, ethanol production from glucose by BW21 at pH 5.2 in OUM1 was essentially complete after 48 h and exceeded that of the parent (strain P2) in LB medium. Thus this new strain, together with the novel minimal medium optimized for production of ethanol by this organism from inexpensive reagents, provide a significant advance in the goal of generating affordable, renewable energy sources from biomass.

REFERENCES

It is believed that a review of the references will increase appreciation of the present invention. The following documents are referred to throughout the present disclosure by a number as indicated below.

[1] *Biobased Industrial Products, Priorities for Research and Commercialization*; Arntzen, C. E.; Dale B. E. (co-chairs). National Academy Press: Washington, D.C. 1999.
[2] Zaldivar, J.; Nielsen J.; Olson L. Fuel Ethanol Production from Lignocellulose: a Challenge for Metabolic Engineering and Process Integration. *Appl. Microbiol. Biotechnol.* 2001, 56, 17-34.
[3] Von Sivers M.; Zacchi G.; Olson L.; Hahn-Hägerdal B. Cost Analysis of Ethanol from Willow Using Recombinant *Escherichia coli. Biotechnol. Frog.* 1994, 10, 555-560
[4] Wyman, C. E. Potential Synergies and Challenges in Refining Cellulosic Biomass to Fuels, Chemicals, and Power. *Biotechnol. Frog.* 2003, 19, 254-262.
[5] Ohta, K.; Beall D. S.; Mejia J. P.; Shanmugan K. T.; Ingram L. O. Metabolic Engineering of *Klebsiella oxytoca* M5A1 for Ethanol Production from Xylose and *Glucose. Appl. Environ. Microbiol.* 1991, 57, 2810-2815.
[6] Wood, B. E.; Ingram L. O. Ethanol Production from Cellobiose, Amorphous Cellulose and Crystalline Cellulose by Recombinant *Klebsiella oxytoca* Containing Chromosomally Integrated *Zymomonas mobilis* Genes for Ethanol Production and Plasmids Expressing Thermostable Cellulase Genes from *Clostridium thermocellum. Appl. Environ. Microbiol.* 1992, 58, 2103-2110.
[7] Bothast, R. J.; Saha B.; Flosenzier A. V.; Ingrain L. O. Fermentation of L-arabinose D-xylose and D-glucose by Ethanologenic Recombinant *Klebsiella oxytoca* strain P2. *Biotechnol Lett.* 1994, 16, 401-406.
[8] Doran J. B.; Aldrich H. C.; Ingram L. O. Saccharification and Fermentation of Sugar-cane Bagasse by *Klebsiella oxytoca* P2 Containing Chromosomally Integrated Genes Encoding the *Zymomonas mobilis* Ethanol Pathway. *Biotechnol. Bioengin.* 1994, 44, 240-247.
[9] Brooks, T. A.; Ingram L. O. Conversion of Mixed Waste Office Paper to Ethanol by Genetically Engineered *Klebsiella oxytoca* strain P2. *Biotechnol. Frog.* 1995, 11, 619-625.
[10] Wood, B. E.; Aldrich H. C.; Ingram L. O. Ultrasound Stimulates Ethanol Production During the Simultaneous Saccharification and Fermentation of Mixed Waste Office Paper. *Biotechnol. Frog.* 1997, 13, 232-237.
[11] Ohta, K.; Beall D. S.; Mejia J. P.; Shanmugam K. T.; Ingram L. O. Genetic Improvement of *Escherichia coli* for Ethanol Production: Chromosomal Integration of *Zymomonas mobilis* Genes Encoding Pyruvate Decarboxylase and Alcohol Dehydrogenase II. *Appl. Environ. Microbial.* 1991, 57, 893-900.
[12] Linsay, S. E.; Bothast R. J.; Ingram L. O. Improved Strains of Recombinant *Escherichia coli* of Ethanol Production from Sugar Mixtures. *Appl. Microbiol. Biotechnol.* 1995, 43, 70-75.
[13] Yomano, L. P.; York S. W.; Ingram L. O. Isolation and Characterization of Ethanol Tolerant Mutants of *Escherichia coli* KO11 for Fuel Ethanol Production. *J. Ind. Microbiol.* 1998, 20, 132-138.
[14] Burchhardt, G.; Ingram L. O. Conversion of Xylan to Ethanol by Ethanologenic Strains of *Escherichia coli* and *Klebsiella oxytoca. Appl. Environ. Microbiol.* 1992, 58, 1128-1133.
[15] Qian Y.; Yomano L. P.; Preston J. F.; Aldrich H. C.; Ingrain L. O. Cloning, Characterization, and Functional Expression of the *Klebsiella oxytoca* Xylodextrin Utilization Operon (xynTB) in *Escherichia coli. Appl. Environ. Microbiol.* 2003, 69, 5957-5967
[16] Kadam, K L.; Newman M. M. Development of a Low-cost Fermentation Medium for Ethanol Production from Biomass. *Appl. Microbiol. Biotechnol.* 1997, 47, 625-629.
[17] Ingram, L. O.; Gomez P. F.; Lai X.; Moniruzzaman M.; Wood B. E.; Yomano L. P.; York S. W. Metabolic Engineering of Bacteria for Ethanol Production. *Biotechnol. Bioengin.* 1998, 58, 204-214.
[18] Zhang, J.; Greasham R. Chemically Defined Media for Commercial Fermentations. *Appl. Microbial. Biotechnol.* 1999, 51, 407-421.
[19] Øskov, I. In Bergey's *Manual of Systematic Bacteriology*, Vol. 1, Kreig, N. R.; Holt J. G. Eds.; Williams and Wilkins, Baltimore, Md., 1984.461-465.
[20] Underwood, S. A; Thou S.; Causey T. B.; Yomano L. P.; Shanmugam K. T.; Ingram L. O. Genetic Changes to Optimize Carbon Partitioning Between Ethanol and Biosynthesis in Ethanologenic *Escherichia coli. Appl. Environ. Microbiol.* 2002, 68, 1715-1727.
[21] Posfai, G.; Koob M.; Kirkpatrick H. A.; Blattner F. R. Versatile Insertion Plasmids for Targeted Genome Manipulations in Bacteria: Isolation, Deletion, and Rescue of the Pathogenicity Island LEE of the *Escherichia coli* O157:H7 Genome. *J. Bacterial.* 1997, 179, 4426-4428.

[22] Datsenko, K A.; Wanner B. L. One-step Inactivation of Chromosomal Genes in *Escherichia coli* K-12 Using PCR Products. *PNAS.* 2000, 97, 6640-6645.

[23] Bolndelet-Rouault, M. H.; Weiser J.; Lebrihi A.; Branny P.; Pernodet J. 1. Antibiotic Resistance Gene Cassette Derived from the Ω Interposon for Use in *E. coli* and *Streptomyces. Gene* 1997, 190, 315-317.

[24] *Current Protocols in Molecular Biology.* Ausubel, F. M.; Brent R.; Kingston R. E.; Moore D. D; Deidman J. G.;. Smith J. A; Struhl K Eds.; John Wiley & Sons, Inc.: New York, N.Y. 1987.

[25] Miller, J. H. *A Short Course in Bacterial Genetics: a Laboratory Manual and Handbook for Escherichia coli and Related Bacteria*; Cold Spring Harbor Laboratory Press: Plainview, N.Y. 1992.

[26] Sambrook, J.; Russell D. W. Molecular Cloning: a Laboratory Manual; Cold Spring Harbor Laboratory Press: Cold Spring Harbor, N.Y., 2001.

[27] Martinez-Morales, F.; Borges A. C.; Martinez A.; Shanmugam K. T.; Ingram L. O. Chromosomal Integration of Heterologous DNA in *Escherichia coli* with Precise Removal of Markers and Replicons Used During Construction. *J. Bacteriol.* 1999, 181, 7143-7148.

[28] Zhou S.; Causey T. B.; Hasona A.; Shanmugam K. T.; Ingram L. O. Production of Optically Pure D-Lactic Acid in Mineral Salts Medium by Metabolically Engineered *Escherichia coli* W3110. *Appl. Environ Microbiol.* 2003, 69, 399-407

[29] Causey, T. B.; Shanmugam K. T.; Yomano L. P.; Ingram L. O. Engineering *Escherichia coli* for Efficient Conversion of Glucose to Pyruvate. *PNAS.* 2004, 101, 2235-2240.

[30] Neidhardt, F. C.; Bloch P. L.; Smith D. F. Culture Media for Enterobacteria. *J. Bacteriol.* 1974, 119, 736-747.

[30] Scopes, R. K. An Iron-Activated Alcohol Dehydrogenase. *FEBS Lett.* 1983, 156, 303-306.

[32] Martinez, A.; York S. W.; Yomano L. P.; Pineda V. L.; Davis F. C.; Shelton J. C.; Ingram L. O. Biosynthetic Burden and Plasmid Burden Limit Expression of Chromosomally Integrated Heterologous Genes (pdc, adhB) in *Escherichia coli. Biotechnol Prog.* 1999, 15, 891-897.

[33] Underwood, S. A.; Buszko M. L.; Shanmugam K. T.; Ingram L. O. Flux Through Citrate Synthase Limits the Growth of Ethanologenic *Escherichia coli* KO11 During Xylose Fermentation. *Appl. Envron. Microbiol.* 2002, 68, 1071-1081.

[34] Beall, D. S., Ohta K., Ingram L. O. Parametric Studies of Ethanol Production from Xylose and Other Sugars by Recombinant *Escherichia coli. Biotechnol. Bioeng.* 1991, 38, 296-303.

[35] Blomqvist, K.; Nikkola M.; Lehtovaara P.; Suihko M.; Airaksinen U.; Strå by K B.; Knowles J. K.; Penttila M. E. Characterization of the 2,3-butanediol Operons from *Klebsiella terrigena* and *Enterobacter aerogenes. J. Bacteriol* 1993, 175, 1392-1404.

[36] Zabriskie, D. W.; Armiger W. B.; Phillips D. H.; Albano P. A. *Traders Guide to Fermentation Media Formulation; Traders Protein.* Memphis, Tenn. 1984.

[37] Mayer, D.; Schlensog V.; Bock A. Identification of the Transcriptional Activator Controlling the Butanediol Fermentation Pathway in *Klebsiella terrigena. J. Bacteriol.* 1995, 177, 5261-5269.

[38] Yang, Y.; Peredelchuk M.; Bennet G. N.; San K. Effect of Variation of *Klebsiella pneumoniae* Acetolactate Synthase Expression on Metabolic Flux Redistribution in *Escherichia coli. Biotechnol. Bioengin.* 2000, 69, 150-159.

[39] Tolan, J. S.; Finn, R. K Fermentation of D-Xylose to Ethanol by Genetically Modified *Klebsiella planticola. Appl. Environ. Microbiol.* 1987, 53, 2039-2044

[40] Washington University *Klebsiella pneumoniae* genome sequencing project home page. http://genome.wustl.edu/projects/bacterial/kpneumoniae (Accessed November 2003)

[41] Teixeira de Mattos, M. J.; Neijssel O. M. Bioenergetic Consequences of Microbial Adaptation to Low-nutrient Environments. *J. Biotechnol.* 1997, 59, 117-126.

[42] Nieves, R. A.; Ehrman C. I.; Adney W. S.; Elander R. T.; Himmel M. E. Technical Communication Survey and Analysis of Commercial Cellulase Preparations Suitable for Biomass Conversion to Ethanol. *World J. Microbiol. Biotechnol.* 1998, 14, 301-304.

[43] Johansen, L.; Bryn K.; Størmer F. C. Physical and Biochemical Role of the Butanediol Pathway in *Aerobacter (Enterobacter) aerogenes. J. Bacteriol.* 1975, 123, 1124-1130.

INCORPORATION BY REFERENCE

All patents, published patent applications and other references disclosed herein are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A recombinant host cell suitable for degrading a saccharide comprising:

(a) a heterologous polynucleotide sequence that codes for an enzyme that converts sugars to ethanol, wherein said host cell expresses said heterologous polynucleotide sequence at a sufficient functional level so as to facilitate production of ethanol as a primary fermentation product by said cell; and (b) a mutation in at least one polynucleotide sequence that codes for a protein in a metabolic pathway in said cell that produces a product other than ethanol from sugars, wherein said mutation results in increased ethanol production by said cell, as compared to ethanol production by the cell in the absence of said mutation;

wherein the recombinant host cell is a Gram-negative bacterium selected from the group consisting of *Klebsiella oxytoca* strains P2 (ATCC 55307), BW15 (NRRLB-30857), BW19 (NRRLB-30858), and BW21 (NRRLB-30859).

2. The recombinant host cell according to claim 1, wherein said product other than ethanol is selected from the group consisting of formate, lactate, succinate, acetate, acetoin, butanediol, 2,3-butanediol, xylitol, butyrate, pyruvate, proprionate, isopropyl alcohol, 1-propanol, 2-propanol, propanediol, citrate, glutamate, and acetone.

3. A method for producing ethanol from a source of saccharide comprising contacting said source with a recombinant host cell of claim 1, to thereby produce ethanol from a source of saccharide.

4. An isolated nucleic acid molecule comprising the nucleotide sequence set forth in SEQ ID NO:3 or 4.

5. An isolated nucleic acid molecule which encodes a polypeptide comprising the amino acid sequence set forth in SEQ ID NO: 6 or 7.

6. An isolated nucleic acid molecule comprising the nucleotide sequence set forth in SEQ ID NO:5 or 8.

7. A system optimized for ethanol production from an oligosaccharide source by the recombinant host cell of claim 1 comprising:
   (a) a selected medium that supports optimal growth and ethanol production by said host cell under selected conditions;
   (b) an oligosaccharide source; and
   (c) the recombinant host cell of claim 1.

8. A kit comprising a recombinant host cell according to claim 1, packaged with instructions for using the recombinant host cell to produce ethanol from a source of saccharide.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctgaatcgg gtcaacattt                                              20
```

-continued

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttcggtttg tccaggtagt                                               20

<210> SEQ ID NO 3
<211> LENGTH: 780
<212> TYPE: DNA
<213> ORGANISM: Klebsiella oxytoca

<400> SEQUENCE: 3
atgaaccatt ctgttgaatg ctcttgtgaa gagagcctgt gtgaaactct acgaggattt    60
tccgcgcaac atcccgatag cgtcatctac cagacctctc tgatgagcgc gctgcttagc   120
ggcgtttatg aaggtaatac gaccatcgcc gatttgctca cccacggtga tttcggcctc   180
gggaccttta tgaactggaa cggcgagctg atcgcgttta gcagtgaagt ttaccagctg   240
cgcgccgacg gcagcgcccg caaagcccgt atggaacagc gtacgccgtt cgcggtgatg   300
acctggtttc agccgcagta tcgcaaaacg ttcgataaac cggtcagccg cgaacagctg   360
cacaacatca tcgaccagca aatcccgtcg gacaatctgt tctgcgccct gcgtattaac   420
ggccattttc gccacgccca tacccgcacg gtaccgcgcc agacgccgcc ctaccgggcg   480
atgaccgacg tactcgacga ccagccggtt tttcgcttca ccagcgcga ggggtcctg    540 gttgggttca gaacgccgca gcatatgcag ggcattaacg tggccggcta ccacgaacac   600
ttcatcaccg atgaccgcca gggcggcggc catctgctcg attatcagct cgaccacggc   660
gtgctgacct ttggcgagat ccacaaattg atgattgacc ttcctgccga tagcgccttc   720
ctgcaggcgg atctgcatcc agacaatctt gatgccgcca ttcgctcagt cgaaaactaa   780

<210> SEQ ID NO 4
<211> LENGTH: 359
<212> TYPE: DNA
<213> ORGANISM: Klebsiella oxytoca

<400> SEQUENCE: 4
gtggataatc aacatcaacc gcgccagtgg gcgcacggcg ccgacctcat cgtcagccag    60
cttgaggccc agggagtacg ccaggtgttc ggcattccgg gggccaaaat cgataaagtc   120
ttcgattcgc tgctcgactc ctccattcgc attatcccgg tgcgccacga agccaacgcc   180
gcctttatgg ccgccgcggt tggccgcatc accggcaaag cgggcgtcgc gctggtcacg   240
tccggaccgg gctgctctaa cctgattacc gggatggcaa cggccaatag cgagggcgac   300
ccggtggtgg cgctgggcgg cgcggtaaaa cgcgccgata agccaaaaca ggtccatca    359

<210> SEQ ID NO 5
<211> LENGTH: 433
<212> TYPE: DNA
<213> ORGANISM: Klebsiella oxytoca

<400> SEQUENCE: 5
gctgaatcgg gtcaacattt atttaacctt tctgatattc gttgaacgag gaagtgggca    60
atgaaccatt ctgttgaatg ctcttgtgaa gagagcctgt gtgaaactct acgaggattt   120
tccgcgcaac atcccgatag cgtcatctac cagacctctc tgatgagcgc gctgcttagg   180

```
gtaccgagct cgaattcccg cgcccgatga attgatccga agttcctatt ctctagaaag    240
tataggaact tcgaattgtc gacaagctcc ccggttggcc gcatcaccgg caaagcgggc    300
gtcgcgctgg tcacgtccgg accgggctgc tctaacctga ttaccgggat ggcaacggcc    360
aatagcgagg cgacccggt ggtggcgctg gcgcgcggt aaaacgcgcc gataaagcca    420
aacaggtcca tca    433
```

<210> SEQ ID NO 6
<211> LENGTH: 259
<212> TYPE: PRT
<213> ORGANISM: Klebsiella oxytoca

<400> SEQUENCE: 6

```
Met Asn His Ser Val Glu Cys Ser Cys Glu Glu Ser Leu Cys Glu Thr
  1               5                  10                  15

Leu Arg Gly Phe Ser Ala Gln His Pro Asp Ser Val Ile Tyr Gln Thr
             20                  25                  30

Ser Leu Met Ser Ala Leu Leu Ser Gly Val Tyr Glu Gly Asn Thr Thr
         35                  40                  45

Ile Ala Asp Leu Leu Thr His Gly Asp Phe Gly Leu Gly Thr Phe Asn
     50                  55                  60

Glu Leu Asp Gly Glu Leu Ile Ala Phe Ser Ser Glu Val Tyr Gln Leu
 65                  70                  75                  80

Arg Ala Asp Gly Ser Ala Arg Lys Ala Arg Met Glu Gln Arg Thr Pro
                 85                  90                  95

Phe Ala Val Met Thr Trp Phe Gln Pro Gln Tyr Arg Lys Thr Phe Asp
            100                 105                 110

Lys Pro Val Ser Arg Glu Gln Leu His Asn Ile Ile Asp Gln Gln Ile
        115                 120                 125

Pro Ser Asp Asn Leu Phe Cys Ala Leu Arg Ile Asn Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Gln Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asp Leu His Pro Asp Asn Leu Asp Ala Ala Ile Arg Ser
                245                 250                 255

Val Glu Asn
```

<210> SEQ ID NO 7
<211> LENGTH: 119
<212> TYPE: PRT
<213> ORGANISM: Klebsiella oxytoca

<400> SEQUENCE: 7

```
Met Asp Asn Gln His Gln Pro Arg Gln Trp Ala His Gly Ala Asp Leu
  1               5                  10                  15

Ile Val Ser Gln Leu Glu Ala Gln Gly Val Arg Gln Val Phe Gly Ile
```

```
            20                  25                  30
Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His
        115

<210> SEQ ID NO 8
<211> LENGTH: 5844
<212> TYPE: DNA
<213> ORGANISM: Klebsiella oxytoca

<400> SEQUENCE: 8
gctgaatcgg gtcaacattt atttaacctt tctgatattc gttgaacgag gaagtgggca        60
atgaaccatt ctgttgaatg ctcttgtgaa gagagcctgt gtgaaactct acgaggattt       120
tccgcgcaac atcccgatag cgtcatctac cagacctctc tgatgagcgc gctgcttagg       180
gtaccgagct cgaattcccg cgcccgatga attgatccga agttcctatt ctctagaaag       240
tataggaact tcgaattgtc gacaagctag cttgcatgcc tgcaggtcga ctctagagga       300
tccccgtact atcaacaggt tgaactgcgg atcttgcggc ccgcgtcagc ttgatcaagg       360
gttggtttgc gcattcacag ttctccgcaa gaattgattg ctccaattc ttggagtggt       420 gaatccgtta gcgaggtgcc gccggcttcc attcaggtcg aggtggcccg gctccatgca       480
ccgcgacgca acgcggggag gcagacaagg tatagggcgg cgcctacaat ccatgccaac       540
ccgttccatg tgctcgccga ggcggcataa atcgccgtga cgatcagcgg tccagtgatc       600
gaagttaggc tggtaagagc cgcgagcgat ccttgaagct gtccctgatg gtcgtcatct       660
acctgcctgg acagcatggc ctgcaacgcg gcatcccga tgccgccgga agcgagaaga       720
atcataatgg ggaaggccat ccagcctcgc gtcgcgaacg ccagcaagac gtagcccagc       780
gcgtcggccg ccatgccggc gataatggcc tgcttctcgc cgaaacgttt ggtggcggga       840
ccagtgacga aggcttgagc gagggcgtgc aagattccga ataccgcaag cgacaggccg       900
atcatcgtcg cgctccagcg aaagcggtcc tcgccgaaaa tgacccagag cgctgccggc       960
acctgtccta cgagttgcat gataaacaag acagtcataa gtgcggcgac gatagtcatg      1020
ccccgcgccc accggaagga gctgactggg ttgaaggctc tcaagggcat cggtcggcgc      1080
tctcccttat gcgactcctg cattaggaag cagcccagta gtaggttgag gccgttgagc      1140
accgccgccg caaggaatgg tgcatgtaag gagatggcgc ccaacagtcc cccggccacg      1200
gggcctgcca ccatacccac gccgaaacaa gcgctcatga gcccgaagtg gcgagcccga      1260
tcttccccat cggtgatgtc ggcgatatag cgccagcaa ccgcacctgt ggcgccggtg       1320
atgccggcca cgatgcgtcc ggcgtagaga atccacagga cgggtgtggt cgccatgatc      1380
gcgtagtcga tagtggctcc aagtagcgaa gcgagcagga ctgggcggcg gccaaagcgg      1440
tcggacagtg ctccgagaac gggtgcgcat agaaattgca tcaacgcata tagcgctagc      1500
agcacgccat agtgactggc gatgctgtcg gaatggacga tatcccgcaa gaggcccggc      1560
```

```
agtaccggca taaccaagcc tatgcctaca gcatccaggg tgacggtgcc gaggatgacg   1620
atgagcgcat tgttagattt catacacggt gcctgactgc gttagcaatt taactgtgat   1680
aaactaccgc attaaagcta gcttatcgat gataagctgt caaacatgag aattgacgcg   1740
cgatgaattg atccgaagtt cctattctct agaaagtata ggaacttcga attgtcgaca   1800
agctccccgg ttggccgcat caccggcaaa gcgggcgtcg cgctggtcac gtccggaccg   1860
ggctgctcta acctgattac cgggatggca acggccaata gcgagggcga cccgtggtg    1920 gcgctgggcg cgcggtaaaa cgcgccgata agccaaaca ggtccatcaa agggcgaatt    1980
ctgcagatat ccatcacact ggcggccgct cgagcatgca tctagagggc ccaattcgcc   2040
ctatagtgag tcgtattaca attcactggc cgtcgtttta caacgtcgtg actgggaaaa   2100
ccctggcgtt acccaactta atcgccttgc agcacatccc cctttcgcca gctggcgtaa   2160
tagcgaagag gcccgcaccg atcgcccttc ccaacagttg cgcagcctga atggcgaatg   2220
ggacgcgccc tgtagcggcg cattaagcgc ggcgggtgtg gtggttacgc gcagcgtgac   2280
cgctacactt gccagcgccc tagcgcccgc tcctttcgct ttcttccctt cctttctcgc   2340
cacgttcgcc ggctttcccc gtcaagctct aaatcggggg ctccctttag ggttccgatt   2400
tagagcttta cggcacctcg accgcaaaaa acttgatttg ggtgatggtt cacgtagtgg   2460
gccatcgccc tgatagacgg ttttttcgcc ctttgacgttg gagtccacgt tctttaatag   2520
tggactcttg ttccaaactg gaacaacact caaccctatc gcggtctatt cttttgattt   2580 ataaggatt ttgccgattt cggcctattg gttaaaaaat gagctgattt aacaaattca    2640
gggcgcaagg gctgctaaag gaaccggaac acgtagaaag ccagtccgca gaaacggtgc   2700
tgaccccgga tgaatgtcag ctactgggct atctggacaa gggaaaacgc aagcgcaaag   2760
agaaagcagg tagcttgcag tgggcttaca tggcgatagc tagactgggc ggttttatgg   2820
acagcaagcg aaccggaatt gccagctggg gcgccctctg gtaaggttgg aagccctgc    2880 aaagtaaact ggatggcttt cttgccgcca aggatctgat ggcgcagggg atcaagatct   2940
gatcaagaga caggatgagg atcgtttcgc atgattgaac aagatggatt gcacgcaggt   3000
tctccggccg cttgggtgga gaggctattc ggctatgact gggcacaaca gacaatcggc   3060
tgctctgatg ccgccgtgtt ccggctgtca gcgcaggggc gcccggttct ttttgtcaag   3120
accgacctgt ccggtgccct gaatgaactg caggacgagg cagcgcggct atcgtggctg   3180
gccacgacgg gcgttccttg cgcagctgtg ctcgacgttg tcactgaagc gggaagggac   3240
tggctgctat tgggcgaagt gccggggcag gatctcctgt catctcgcct tgctcctgcc   3300
gagaaagtat ccatcatggc tgatgcaatg cggcggctgc atacgcttga tccggctacc   3360
tgcccattcg accaccaagc gaaacatcgc atcgagcgag cacgtactcg gatggaagcc   3420
ggtcttgtcg atcaggatga tctggacgaa gagcatcagg ggctcgcgcc agccgaactg   3480
ttcgccaggc tcaaggcgcg catgcccgac ggcgaggatc tcgtcgtgat ccatggcgat   3540
gcctgcttgc cgaatatcat ggtggaaaat ggccgctttt ctggattcaa cgactgtggc   3600
cggctgggtg tggcggaccg ctatcaggac atagcgttgg ataccgtga tattgctgaa    3660 gagcttggcg gcgaatgggc tgaccgcttc ctcgtgcttt acggtatcgc cgctcccgat   3720
tcgcagcgca tcgccttcta tcgccttctt gacgagttct tctgaattga aaaggaaga    3780 gtatgagtat tcaacatttc cgtgtcgccc ttattccctt ttttgcggca ttttgccttc   3840 ctgttttgc tcacccagaa acgctggtga agtaaaaga tgctgaagat cagttgggtg    3900
cacgagtggg ttacatcgaa ctggatctca acagcggtaa gatccttgag agttttcgcc   3960
```

```
ccgaagaacg ttttccaatg atgagcactt ttaaagttct gctatgtcat acactattat    4020
cccgtattga cgccgggcaa gagcaactcg gtcgccgggc gcggtattct cagaatgact    4080
tggttgagta ctcaccagtc acagaaaagc atcttacgga tggcatgaca gtaagagaat    4140
tatgcagtgc tgccataacc atgagtgata acactgcggc caacttactt ctgacaacga    4200
tcggaggacc gaaggagcta accgcttttt tgcacaacat gggggatcat gtaactcgcc    4260
ttgatcgttg ggaaccggag ctgaatgaag ccataccaaa cgacgagagt gacaccacga    4320
tgcctgtagc aatgccaaca acgttgcgca aactattaac tggcgaacta cttactctag    4380
cttcccggca acaattaata gactggatgg aggcggataa agttgcagga ccacttctgc    4440
gctcggccct tccggctggc tggtttattg ctgataaatc tggagccggt gagcgtgggt    4500
ctcgcggtat cattgcagca ctggggccag atggtaagcc ctcccgtatc gtagttatct    4560
acacgacggg gagtcaggca actatggatg aacgaaatag acagatcgct gagataggtg    4620
cctcactgat taagcattgg taactgtcag accaagttta ctcatatata ctttagattg    4680
atttaaaact tcattttaa tttaaaagga tctaggtgaa gatcctttt gataatctca     4740
tgaccaaaat cccttaacgt gagttttcgt tccactgagc gtcagacccc gtagaaaaga    4800
tcaaaggatc ttcttgagat cctttttttc tgcgcgtaat ctgctgcttg caaacaaaaa    4860
aaccaccgct accagcggtg gtttgtttgc cggatcaaga gctaccaact cttttttcga    4920
aggtaactgg cttcagcaga gcgcagatac caaatactgt ccttctagtg tagccgtagt    4980
taggccacca cttcaagaac tctgtagcac cgcctacata cctcgctctg ctaatcctgt    5040
taccagtggc tgctgccagt ggcgataagt cgtgtcttac cgggttggac tcaagacgat    5100
agttaccgga taaggcgcag cggtcgggct gaacggggg ttcgtgcaca cagcccagct    5160
tggagcgaac gacctacacc gaactgagat acctacagcg tgagcattga gaaagcgcca    5220
cgcttcccga agggagaaag gcggacaggt atccggtaag cggcagggtc ggaacaggag    5280
agcgcacgag ggagcttcca gggggaaacg cctggtatct ttatagtcct gtcgggtttc    5340
gccacctctg acttgagcgt cgatttttgt gatgctcgtc agggggggcgg agcctatgga    5400
aaaacgccag caacgcggcc ttttacggt tcctggcctt ttgctggcct tttgctcaca     5460
tgttctttcc tgcgttatcc cctgattctg tggataaccg tattaccgcc tttgagtgag    5520
ctgataccgc tcgccgcagc cgaacgaccg agcgcagcga gtcagtgagc gaggaagcgg    5580
aagagcgccc aatacgcaaa ccgcctctcc ccgcgcgttg gccgattcat taatgcagct    5640
ggcacgacag gtttcccgac tggaaagcgg gcagtgagcg caacgcaatt aatgtgagtt    5700
agctcactca ttaggcaccc caggctttac actttatgct tccggctcgt atgttgtgtg    5760
gaattgtgag cggataacaa tttcacacag gaaacagcta tgaccatgat tacgccaagc    5820
ttggtaccga gctcggatcc acta                                           5844
```